US012747278B2

(12) United States Patent
Chung et al.

(10) Patent No.: US 12,747,278 B2
(45) Date of Patent: Sep. 29, 2026

(54) CHIMERIC ANTIGEN RECEPTOR FOR TREATMENT OF CANCER

(71) Applicants: SMT BIO CO., LTD., Seoul (KR); INDUSTRY-ACADEMIC COOPERATION FOUNDATION, YONSEI UNIVERSITY, Seoul (KR)

(72) Inventors: Yong Yoon Chung, Seoul (KR); In Hye Jung, Seoul (KR)

(73) Assignees: SMT BIO CO., LTD., Seoul (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 943 days.

(21) Appl. No.: 17/998,233

(22) PCT Filed: May 7, 2021

(86) PCT No.: PCT/KR2021/005721

§ 371 (c)(1),
(2) Date: Nov. 8, 2022

(87) PCT Pub. No.: WO2021/225399

PCT Pub. Date: Nov. 11, 2021

(65) Prior Publication Data

US 2023/0227525 A1 Jul. 20, 2023

(30) Foreign Application Priority Data

May 8, 2020 (KR) ........................ 10-2020-0055248

(51) Int. Cl.

| | |
|---|---|
| ***C07K 14/725*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/705*** | (2006.01) |
| ***C07K 16/30*** | (2006.01) |
| *A61K 38/00* | (2006.01) |
| *A61K 39/00* | (2006.01) |

(52) U.S. Cl.

CPC .......... *C07K 14/7051* (2013.01); *A61K 40/11* (2025.01); *A61K 40/31* (2025.01); *A61K 40/4204* (2025.01); *A61K 40/4266* (2025.01); *A61P 35/00* (2018.01); *C07K 14/70514* (2013.01); *C07K 14/70517* (2013.01); *C07K 14/70521* (2013.01); *C07K 14/70532* (2013.01); *C07K 14/70578* (2013.01); *C07K 14/70589* (2013.01); *C07K 14/70596* (2013.01); *C07K 16/3007* (2013.01); *A61K 38/00* (2013.01); *A61K 39/00* (2013.01); *A61K 2239/50* (2023.05)

(58) Field of Classification Search

CPC ..... C07K 14/7051; A61K 40/31; A61K 40/11
See application file for complete search history.

(56) References Cited

U.S. PATENT DOCUMENTS

| | | | |
|---|---|---|---|
| 7,273,608 | B2 | 9/2007 | Yazaki et al. |
| 2008/0096810 | A1 | 4/2008 | Fox et al. |

FOREIGN PATENT DOCUMENTS

| | | | |
|---|---|---|---|
| KR | 10-2017-0090506 | A | 8/2017 |
| KR | 10-2017-0134331 | A | 12/2017 |
| KR | 10-2018-0021137 | A | 2/2018 |

OTHER PUBLICATIONS

Raskov, (2021) 124:359-367; https://doi.org/10.1038/s41416-020-01048-4.*

Zhang, Molecular Therapy vol. 25 No May 5, 2017, 1248-1258).*

Neumaier (Cancer Research 50. 2128-2134. Apr. 1, 1990).*

Cha, The Journal of Immunology, vol. 204, Issue 1 Supplement, May 1, 2020, p. 239.25, https://doi.org/10.4049/jimmunol.204.Supp.239.25.*

Szekanecz (2011, 2nd International Cancer Immunotherapy and Immunomonitoring Conference, Budapest, Hungary, Abstract book , Redefining Cancer Therapy).*

Polli, Journal of Pharmaceutical Sciences, vol. 108, Issue 1, Jan. 2019, pp. 674-691.*

Yazaki, Protein Engineering, Design & Selection vol. 17 No. 5 pp. 481-489, 2004.*

Oldham (2017, Expert Opinion on Biological Therapy, 17:8, 961-978, DOI: 10.1080/14712598.2017.1339687).*

David L. Porter, M.D. et al., “Chimeric Antigen Receptor-Modified T Cells in Chronic Lymphoid Leukemia”, The New England Journal of Medicine, Aug. 25, 2011, pp. 725-733.

Michael Kalos et al., “T Cells with Chimeric Antigen Receptors Have Potent Antitumor Effects and Can Establish Memory in Patients with Advance Leukemia”, Sci Transl Med 3, 2011, pp. 1-11.

Shannon L. Maude, M.D., Ph. D et al., “Chimeric Antigen Receptor T Cells for Sustained Remissions in Leukemia”, The New England Journal of Medicine, Oct. 16, 2014, pp. 1507-1517.

Joseph P. Remington, Ph. M., “The Modes of making and dispensing officinal, unofficinal, and extemporaneous preparations, with descriptions of their properties, uses and doses”, The Practice of Pharmacy, 1892.

International Search Report for PCT/KR2021/005721 dated Aug. 23, 2021.

* cited by examiner

*Primary Examiner* — Valarie E Bertoglio
(74) *Attorney, Agent, or Firm* — Sughrue Mion, PLLC

(57) ABSTRACT

The present invention relates to a novel chimeric antigen receptor and to a pharmaceutical composition for preventing or treating containing the same.

1 Claim, 8 Drawing Sheets

Specification includes a Sequence Listing.

[FIG. 1]

scFv-CD8 hinge and TM-4-1BB-CD3zeta

[FIG. 2]

EF-1alpha promoter-signal peptide-scFv-CD8 hinge and TM-4-1BB-CD3zeta-T2A-EGFRt

[FIG. 3]
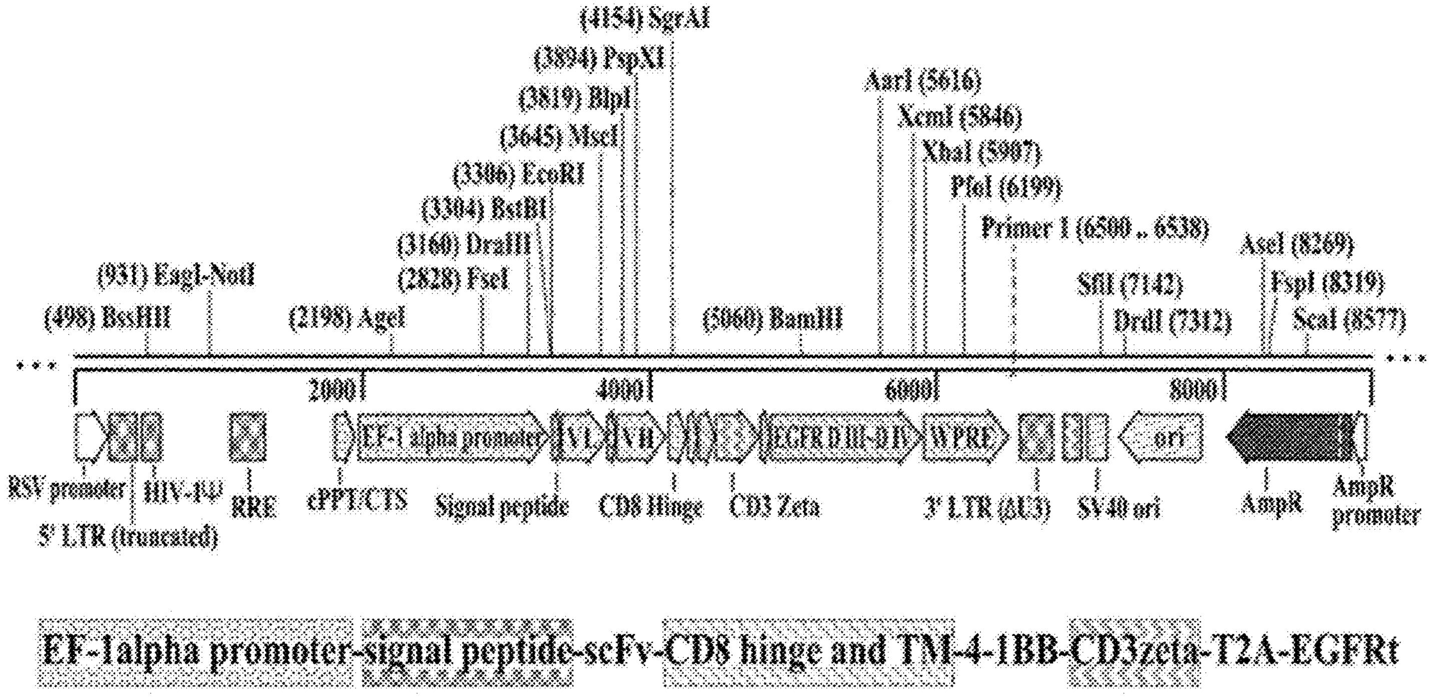

[FIG. 4]
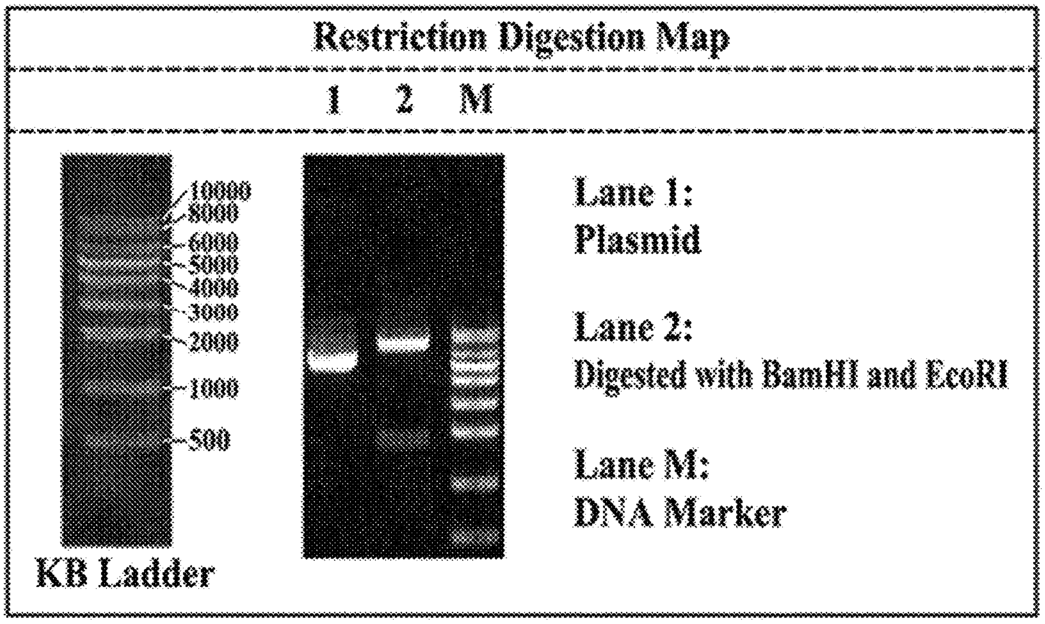

[FIG. 5]
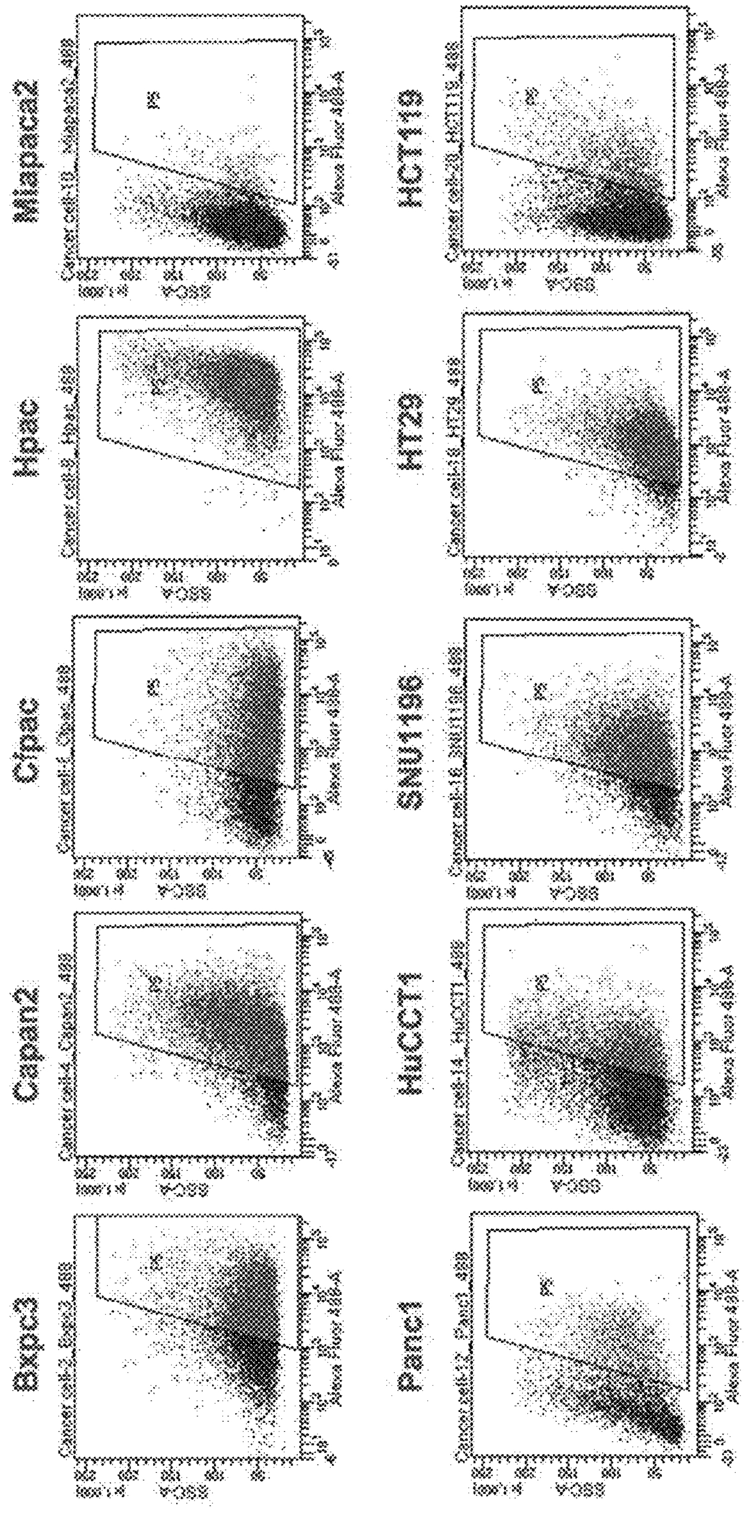

[FIG. 6]
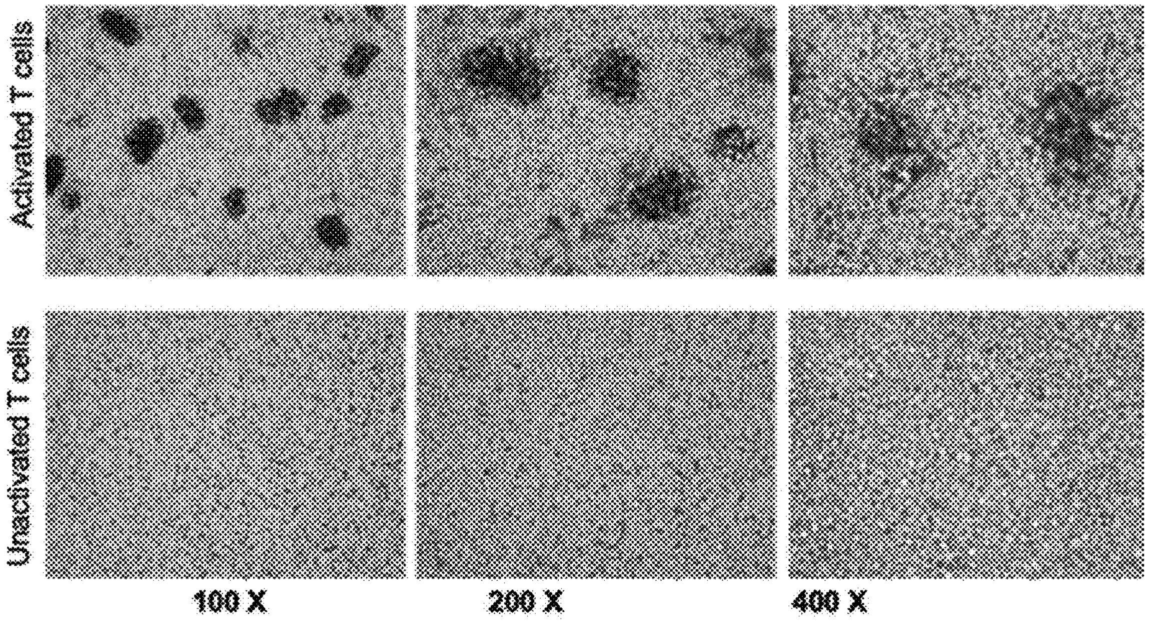
[FIG. 7]
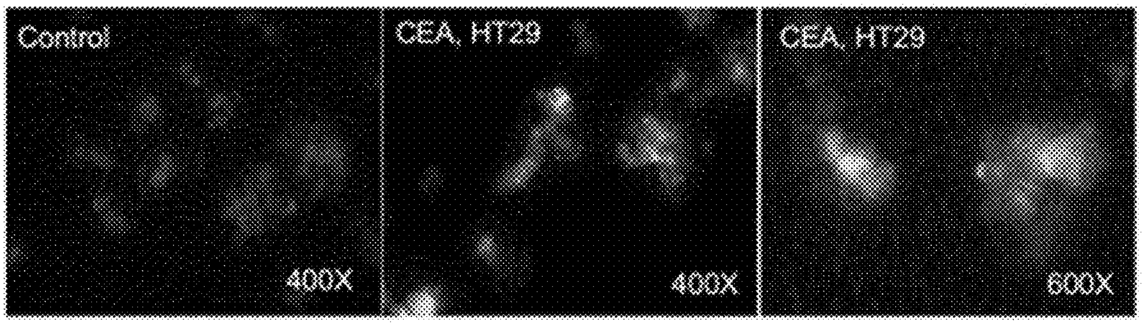

[FIG. 8]
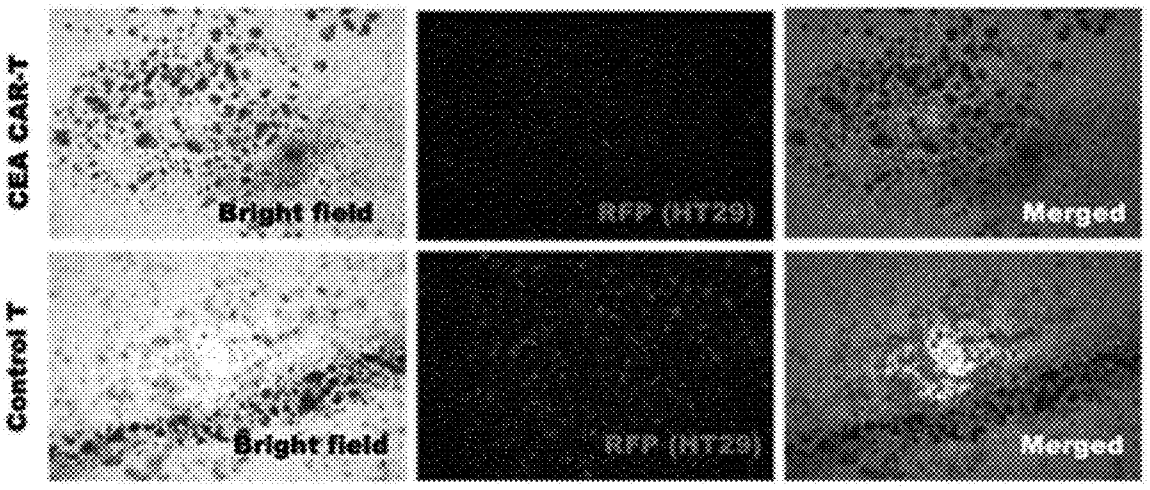

[FIG. 9]
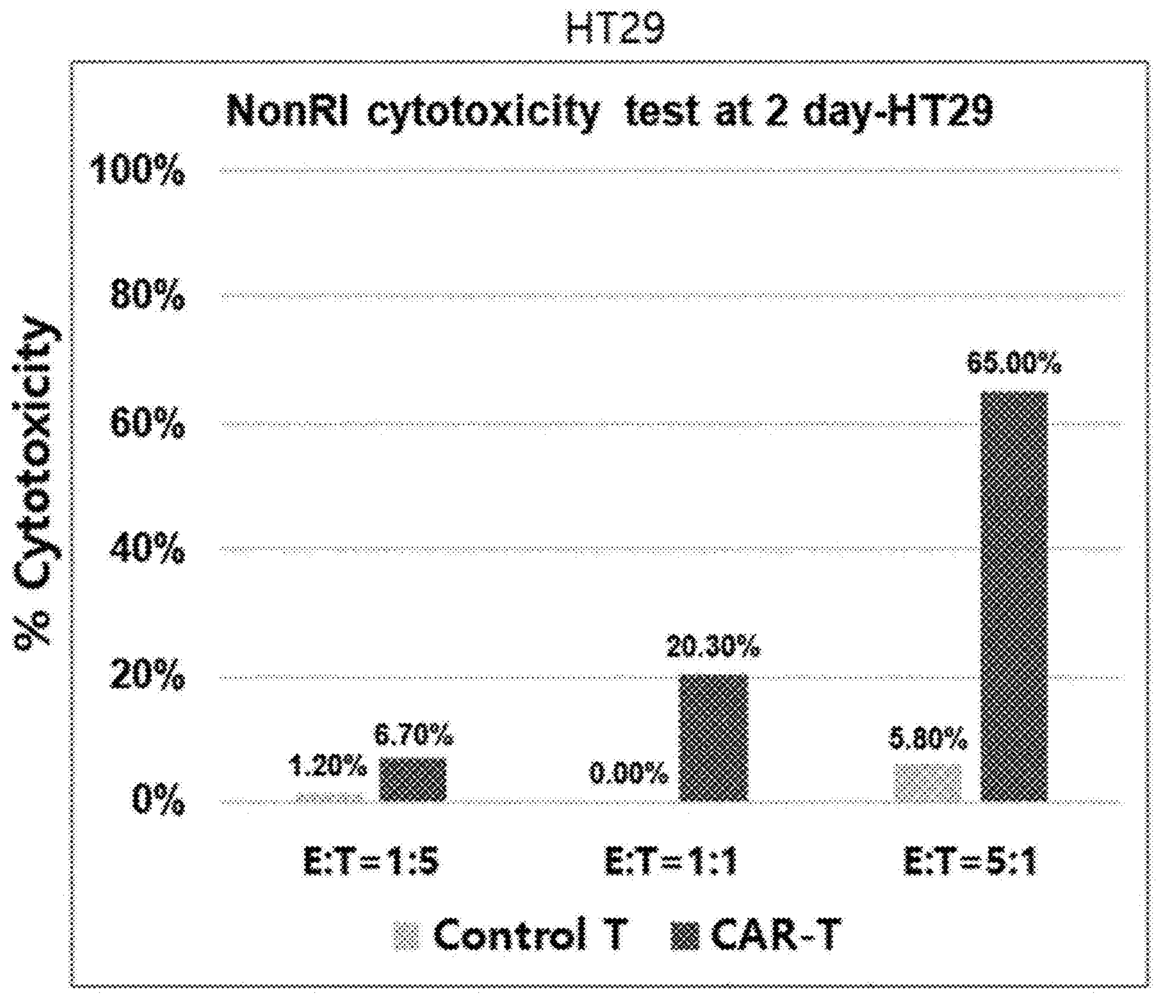

[FIG. 10]
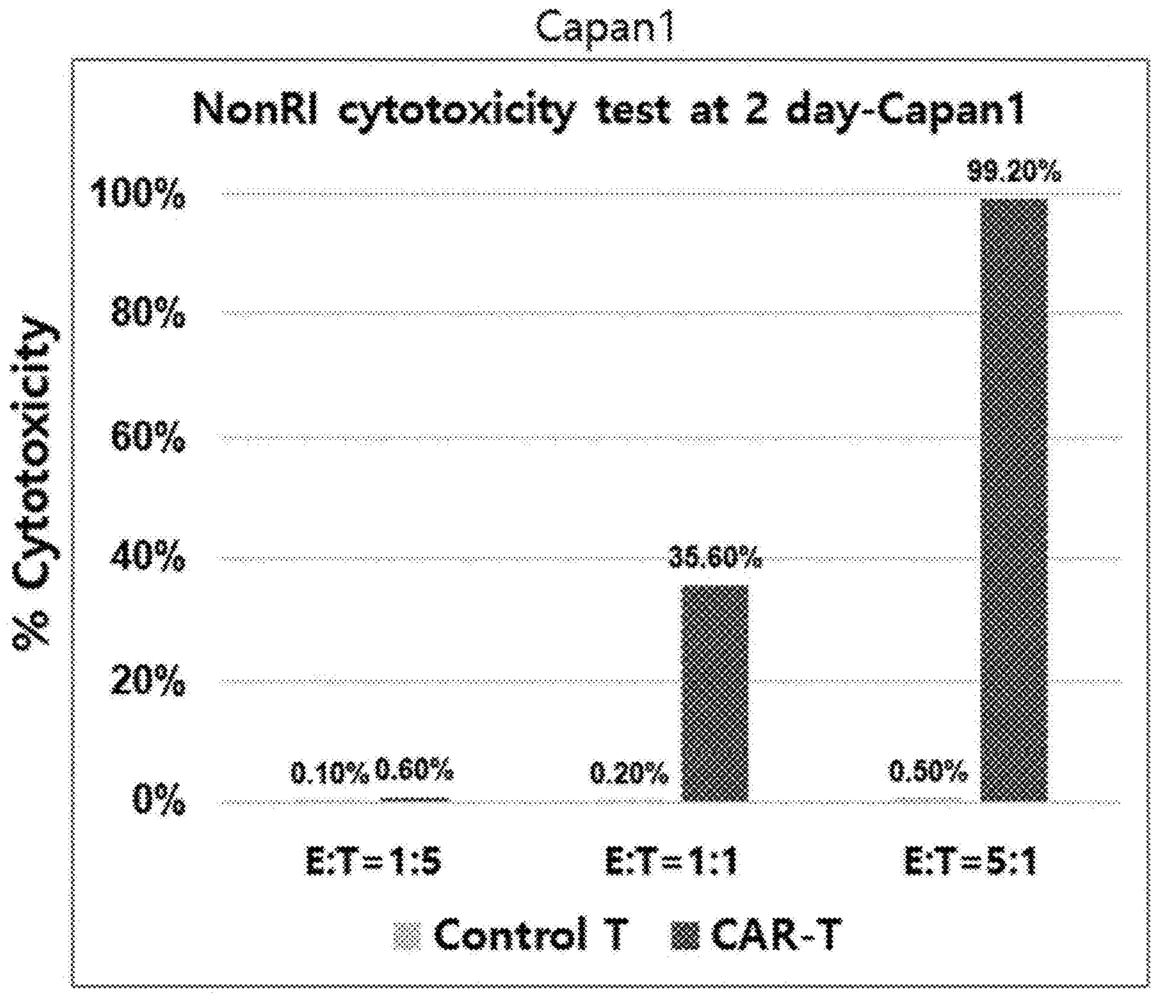

SEQUENCE LISTING

```
<160> NUMBER OF SEQ ID NOS: 20

<210> SEQ ID NO 1
<211> LENGTH: 111
<212> TYPE: PRT
<213> ORGANISM: Artificial Sequence
<220> FEATURE:
<223> OTHER INFORMATION: VH domain

<400> SEQUENCE: 1

Asp Ile Val Leu Thr Gln Ser Pro Ala Ser Leu Ala Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Pro Pro
        35                  40                  45
```

```
Lys Leu Leu Ile Tyr Arg Ala Ser Asn Leu Glu Ser Gly Ile Pro Val
    50                  55                  60

Arg Phe Ser Gly Thr Gly Ser Arg Thr Asp Phe Thr Leu Ile Ile Asp
65                  70                  75                  80

Pro Val Glu Ala Asp Asp Val Ala Thr Tyr Tyr Cys Gln Gln Thr Asn
                85                  90                  95

Glu Asp Pro Tyr Thr Phe Gly Gly Gly Thr Lys Leu Glu Ile Lys
            100                 105                 110


<210> SEQ ID NO 2
<211> LENGTH: 121
<212> TYPE: PRT
<213> ORGANISM: Artificial Sequence
<220> FEATURE:
<223> OTHER INFORMATION: VL domain

<400> SEQUENCE: 2

Glu Val Gln Leu Gln Gln Ser Gly Ala Glu Leu Val Glu Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Ser Lys Tyr Val Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Thr Ser Leu Thr Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Ser Val Thr Val Ser Ser
        115                 120


<210> SEQ ID NO 3
<211> LENGTH: 15
<212> TYPE: PRT
<213> ORGANISM: Artificial Sequence
<220> FEATURE:
<223> OTHER INFORMATION: linker

<400> SEQUENCE: 3

Gly Gly Gly Gly Ser Gly Gly Gly Gly Ser Gly Gly Gly Gly Ser
1               5                   10                  15


<210> SEQ ID NO 4
<211> LENGTH: 45
<212> TYPE: PRT
<213> ORGANISM: Artificial Sequence
<220> FEATURE:
<223> OTHER INFORMATION: hinge region

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

```
<210> SEQ ID NO 5
<211> LENGTH: 24
<212> TYPE: PRT
<213> ORGANISM: Artificial Sequence
<220> FEATURE:
<223> OTHER INFORMATION: transmembrane domain

<400> SEQUENCE: 5

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 6
<211> LENGTH: 42
<212> TYPE: PRT
<213> ORGANISM: Artificial Sequence
<220> FEATURE:
<223> OTHER INFORMATION: co-stimulatory domain

<400> SEQUENCE: 6

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 7
<211> LENGTH: 112
<212> TYPE: PRT
<213> ORGANISM: Artificial Sequence
<220> FEATURE:
<223> OTHER INFORMATION: signal transduction domain

<400> SEQUENCE: 7

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 8
<211> LENGTH: 21
<212> TYPE: PRT
<213> ORGANISM: Artificial Sequence
<220> FEATURE:
<223> OTHER INFORMATION: signal peptide

<400> SEQUENCE: 8

Met Ala Leu Pro Val Thr Ala Leu Leu Leu Pro Leu Ala Leu Leu Leu
1               5                   10                  15

His Ala Ala Arg Pro
```

20

<210> SEQ ID NO 9
<211> LENGTH: 470
<212> TYPE: PRT
<213> ORGANISM: Artificial Sequence
<220> FEATURE:
<223> OTHER INFORMATION: chimeric antigen receptor

<400> SEQUENCE: 9

Asp Ile Val Leu Thr Gln Ser Pro Ala Ser Leu Ala Val Ser Leu Gly
1 5 10 15

Gln Arg Ala Thr Met Ser Cys Arg Ala Gly Glu Ser Val Asp Ile Phe
20 25 30

Gly Val Gly Phe Leu His Trp Tyr Gln Gln Lys Pro Gly Gln Pro Pro
35 40 45

Lys Leu Leu Ile Tyr Arg Ala Ser Asn Leu Glu Ser Gly Ile Pro Val
50 55 60

Arg Phe Ser Gly Thr Gly Ser Arg Thr Asp Phe Thr Leu Ile Ile Asp
65 70 75 80

Pro Val Glu Ala Asp Asp Val Ala Thr Tyr Tyr Cys Gln Gln Thr Asn
85 90 95

Glu Asp Pro Tyr Thr Phe Gly Gly Gly Thr Lys Leu Glu Ile Lys Gly
100 105 110

Gly Gly Gly Ser Gly Gly Gly Gly Ser Gly Gly Gly Gly Ser Glu Val
115 120 125

Gln Leu Gln Gln Ser Gly Ala Glu Leu Val Glu Pro Gly Ala Ser Val
130 135 140

Lys Leu Ser Cys Thr Ala Ser Gly Phe Asn Ile Lys Asp Thr Tyr Met
145 150 155 160

His Trp Val Lys Gln Arg Pro Glu Gln Gly Leu Glu Trp Ile Gly Arg
165 170 175

Ile Asp Pro Ala Asn Gly Asn Ser Lys Tyr Val Pro Lys Phe Gln Gly
180 185 190

Lys Ala Thr Ile Thr Ala Asp Thr Ser Ser Asn Thr Ala Tyr Leu Gln
195 200 205

Leu Thr Ser Leu Thr Ser Glu Asp Thr Ala Val Tyr Tyr Cys Ala Pro
210 215 220

Phe Gly Tyr Tyr Val Ser Asp Tyr Ala Met Ala Tyr Trp Gly Gln Gly
225 230 235 240

Thr Ser Val Thr Val Ser Ser Thr Thr Thr Pro Ala Pro Arg Pro Pro
245 250 255

Thr Pro Ala Pro Thr Ile Ala Ser Gln Pro Leu Ser Leu Arg Pro Glu
260 265 270

Ala Cys Arg Pro Ala Ala Gly Gly Ala Val His Thr Arg Gly Leu Asp
275 280 285

Phe Ala Cys Asp Ile Tyr Ile Trp Ala Pro Leu Ala Gly Thr Cys Gly
290 295 300

Val Leu Leu Leu Ser Leu Val Ile Thr Leu Tyr Cys Lys Arg Gly Arg
305 310 315 320

Lys Lys Leu Leu Tyr Ile Phe Lys Gln Pro Phe Met Arg Pro Val Gln
325 330 335

Thr Thr Gln Glu Glu Asp Gly Cys Ser Cys Arg Phe Pro Glu Glu Glu
340 345 350

Glu Gly Gly Cys Glu Leu Arg Val Lys Phe Ser Arg Ser Ala Asp Ala

```
        355                 360                 365

Pro Ala Tyr Lys Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470


<210> SEQ ID NO 10
<211> LENGTH: 491
<212> TYPE: PRT
<213> ORGANISM: Artificial Sequence
<220> FEATURE:
<223> OTHER INFORMATION: chimeric antigen receptor

<400> SEQUENCE: 10

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
            20                  25                  30

Ala Val Ser Leu Gly Gln Arg Ala Thr Met Ser Cys Arg Ala Gly Glu
        35                  40                  45

Ser Val Asp Ile Phe Gly Val Gly Phe Leu His Trp Tyr Gln Gln Lys
    50                  55                  60

Pro Gly Gln Pro Pro Lys Leu Leu Ile Tyr Arg Ala Ser Asn Leu Glu
65                  70                  75                  80

Ser Gly Ile Pro Val Arg Phe Ser Gly Thr Gly Ser Arg Thr Asp Phe
                85                  90                  95

Thr Leu Ile Ile Asp Pro Val Glu Ala Asp Asp Val Ala Thr Tyr Tyr
            100                 105                 110

Cys Gln Gln Thr Asn Glu Asp Pro Tyr Thr Phe Gly Gly Gly Thr Lys
        115                 120                 125

Leu Glu Ile Lys Gly Gly Gly Gly Ser Gly Gly Gly Gly Ser Gly Gly
    130                 135                 140

Gly Gly Ser Glu Val Gln Leu Gln Gln Ser Gly Ala Glu Leu Val Glu
145                 150                 155                 160

Pro Gly Ala Ser Val Lys Leu Ser Cys Thr Ala Ser Gly Phe Asn Ile
                165                 170                 175

Lys Asp Thr Tyr Met His Trp Val Lys Gln Arg Pro Glu Gln Gly Leu
            180                 185                 190

Glu Trp Ile Gly Arg Ile Asp Pro Ala Asn Gly Asn Ser Lys Tyr Val
        195                 200                 205

Pro Lys Phe Gln Gly Lys Ala Thr Ile Thr Ala Asp Thr Ser Ser Asn
    210                 215                 220

Thr Ala Tyr Leu Gln Leu Thr Ser Leu Thr Ser Glu Asp Thr Ala Val
225                 230                 235                 240

Tyr Tyr Cys Ala Pro Phe Gly Tyr Tyr Val Ser Asp Tyr Ala Met Ala
```

-continued

```
                245                 250                 255

Tyr Trp Gly Gln Gly Thr Ser Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 11
<211> LENGTH: 1410
<212> TYPE: DNA
<213> ORGANISM: Artificial Sequence
<220> FEATURE:
<223> OTHER INFORMATION: chimeric antigen receptor

<400> SEQUENCE: 11

gacatcgtgc tgacacagag ccctgcttct ctggccgtgt ctcttggaca gagggccacc     60

atgtcttgta gagccggcga gagcgtggac atcttcggcg tgggatttct gcactggtat    120

cagcagaagc ccggccagcc tcctaagctg ctgatctaca gagccagcaa cctggaaagc    180

ggcatccctg tgcggtttag cggcacaggc agcagaaccg acttcaccct gatcatcgac    240

cccgtggaag ccgatgatgt ggccacctac tactgccagc agaccaacga ggacccctac    300

acatttggcg gaggcaccaa gctggaaatc aagggtggag gtggcagcgg aggaggtggg    360

tccggcggtg gaggaagcga ggttcagctg cagcagtctg gcgctgaact ggttgaacct    420

ggcgcctctg tgaagctgag ctgtaccgcc agcggcttca acatcaagga cacctacatg    480

cactgggtca agcagaggcc tgagcaggga ctcgagtgga tcggcagaat cgatcccgcc    540

aacggcaaca gcaaatacgt gcccaagttc cagggcaaag ccaccatcac cgccgacacc    600

tctagcaaca cagcctacct gcagctcacc agcctgacct ctgaagatac cgccgtgtac    660
```

```
tactgcgccc ctttcggcta ctacgtgtcc gattacgcca tggcctattg gggccagggc    720

acaagcgtga cagtcagctc taccacgacg ccagcgccgc gaccaccaac accggcgccc    780

accatcgcgt cgcagcccct gtccctgcgc ccagaggcgt gccggccagc ggcgggggc     840

gcagtgcaca cgagggggct ggacttcgcc tgtgatatct acatttgggc ccctctggct    900

ggtacttgcg gggtcctgct gctttcactc gtgatcactc tttactgtaa gcgcggtcgg    960

aagaagctgc tgtacatctt taagcaaccc ttcatgaggc ctgtgcagac tactcaagag   1020

gaggacggct gttcatgccg gttcccagag gaggaggaag gcggctgcga actgagagtg   1080

aagttcagca ggagcgcaga cgcccccgcg tacaagcagg gccagaacca gctctataac   1140

gagctcaatc taggacgaag agaggagtac gatgttttgg acaagagacg tggccgggac   1200

cctgagatgg ggggaaagcc gagaaggaag aaccctcagg aaggcctgta caatgaactg   1260

cagaaagata agatggcgga ggcctacagt gagattggga tgaaaggcga gcgccggagg   1320

ggcaaggggc acgatggcct ttaccagggt ctcagtacag ccaccaagga cacctacgac   1380

gcccttcaca tgcaggccct gccccctcgc                                    1410
```

```
<210> SEQ ID NO 12
<211> LENGTH: 1473
<212> TYPE: DNA
<213> ORGANISM: Artificial Sequence
<220> FEATURE:
<223> OTHER INFORMATION: chimeric antigen receptor

<400> SEQUENCE: 12
```

```
atggccttac cagtgaccgc cttgctcctg ccgctggcct tgctgctcca cgccgccagg     60

ccggacatcg tgctgacaca gagccctgct tctctggccg tgtctcttgg acagagggcc    120

accatgtctt gtagagccgg cgagagcgtg gacatcttcg gcgtgggatt tctgcactgg    180

tatcagcaga agcccggcca gcctcctaag ctgctgatct acagagccag caacctggaa    240

agcggcatcc ctgtgcggtt tagcggcaca ggcagcagaa ccgacttcac cctgatcatc    300

gaccccgtgg aagccgatga tgtggccacc tactactgcc agcagaccaa cgaggacccc    360

tacacatttg gcggaggcac caagctggaa atcaagggtg gaggtggcag cggaggaggt    420

gggtccggcg gtggaggaag cgaggttcag ctgcagcagt ctggcgctga actggttgaa    480

cctggcgcct ctgtgaagct gagctgtacc gccagcggct tcaacatcaa ggacacctac    540

atgcactggg tcaagcagag gcctgagcag ggactcgagt ggatcggcag aatcgatccc    600

gccaacggca acagcaaata cgtgcccaag ttccagggca aagccaccat caccgccgac    660

acctctagca acacagccta cctgcagctc accagcctga cctctgaaga taccgccgtg    720

tactactgcg cccctttcgg ctactacgtg tccgattacg ccatggccta ttggggccag    780

ggcacaagcg tgacagtcag ctctaccacg acgccagcgc cgcgaccacc aacaccggcg    840

cccaccatcg cgtcgcagcc cctgtccctg cgcccagagg cgtgccggcc agcggcgggg    900

ggcgcagtgc acacgagggg gctggacttc gcctgtgata tctacatttg ggcccctctg    960

gctggtactt gcggggtcct gctgctttca ctcgtgatca ctctttactg taagcgcggt   1020

cggaagaagc tgctgtacat ctttaagcaa cccttcatga ggcctgtgca gactactcaa   1080

gaggaggacg gctgttcatg ccggttccca gaggaggagg aaggcggctg cgaactgaga   1140

gtgaagttca gcaggagcgc agacgccccc gcgtacaagc agggccagaa ccagctctat   1200

aacgagctca atctaggacg aagagaggag tacgatgttt tggacaagag acgtggccgg   1260

gaccctgaga tgggggaaa gccgagaagg aagaaccctc aggaaggcct gtacaatgaa    1320
```

```
ctgcagaaag ataagatggc ggaggcctac agtgagattg ggatgaaagg cgagcgccgg   1380

aggggcaagg ggcacgatgg cctttaccag ggtctcagta cagccaccaa ggacacctac   1440

gacgcccttc acatgcaggc cctgcccct cgc                                 1473


<210> SEQ ID NO 13
<211> LENGTH: 352
<212> TYPE: PRT
<213> ORGANISM: Artificial Sequence
<220> FEATURE:
<223> OTHER INFORMATION: EGFRt

<400> SEQUENCE: 13

Met Trp Leu Gln Ser Leu Leu Leu Leu Gly Thr Val Ala Cys Ser Ile
1               5                   10                  15

Ser Arg Lys Val Cys Asn Gly Ile Gly Ile Gly Glu Phe Lys Asp Ser
            20                  25                  30

Leu Ser Ile Asn Ala Thr Asn Ile Lys His Phe Lys Asn Cys Thr Ser
        35                  40                  45

Ile Ser Gly Asp Leu His Ile Leu Pro Val Ala Phe Arg Gly Asp Ser
    50                  55                  60

Phe Thr His Thr Pro Pro Leu Asp Pro Gln Glu Leu Asp Ile Leu Lys
65                  70                  75                  80

Thr Val Lys Glu Ile Thr Gly Phe Leu Leu Ile Gln Ala Trp Pro Glu
                85                  90                  95

Asn Arg Thr Asp Leu His Ala Phe Glu Asn Leu Glu Ile Ile Arg Gly
            100                 105                 110

Arg Thr Lys Gln His Gly Gln Phe Ser Leu Ala Val Val Ser Leu Asn
        115                 120                 125

Ile Thr Ser Leu Gly Leu Arg Ser Leu Lys Glu Ile Ser Asp Gly Asp
    130                 135                 140

Val Ile Ile Ser Gly Asn Lys Asn Leu Cys Tyr Ala Asn Thr Ile Asn
145                 150                 155                 160

Trp Lys Lys Leu Phe Gly Thr Ser Gly Gln Lys Thr Lys Ile Ile Ser
                165                 170                 175

Asn Arg Gly Glu Asn Ser Cys Lys Ala Thr Gly Gln Val Cys His Ala
            180                 185                 190

Leu Cys Ser Pro Glu Gly Cys Trp Gly Pro Glu Pro Arg Asp Cys Val
        195                 200                 205

Ser Cys Arg Asn Val Ser Arg Gly Arg Glu Cys Val Asp Lys Cys Asn
    210                 215                 220

Leu Leu Glu Gly Glu Pro Arg Glu Phe Val Glu Asn Ser Glu Cys Ile
225                 230                 235                 240

Gln Cys His Pro Glu Cys Leu Pro Gln Ala Met Asn Ile Thr Cys Thr
                245                 250                 255

Gly Arg Gly Pro Asp Asn Cys Ile Gln Cys Ala His Tyr Ile Asp Gly
            260                 265                 270

Pro His Cys Val Lys Thr Cys Pro Ala Gly Val Met Gly Glu Asn Asn
        275                 280                 285

Thr Leu Val Trp Lys Tyr Ala Asp Ala Gly His Val Cys His Leu Cys
    290                 295                 300

His Pro Asn Cys Thr Tyr Gly Cys Thr Gly Pro Gly Leu Glu Gly Cys
305                 310                 315                 320

Pro Thr Asn Gly Pro Lys Ile Pro Ser Ile Ala Thr Gly Met Val Gly
                325                 330                 335
```

Ala Leu Leu Leu Leu Leu Val Val Ala Leu Gly Ile Gly Leu Phe Met
340 345 350

<210> SEQ ID NO 14
<211> LENGTH: 1056
<212> TYPE: DNA
<213> ORGANISM: Artificial Sequence
<220> FEATURE:
<223> OTHER INFORMATION: EGFRt

<400> SEQUENCE: 14
atgtggctgc agagcctgct gctcttgggc actgtggcct gcagcatctc tcgcaaagtg 60
tgtaacggaa taggtattgg tgaatttaaa gactcactct ccataaatgc tacgaatatt 120
aaacacttca aaaactgcac ctccatcagt ggcgatctcc acatcctgcc ggtggcattt 180
aggggtgact ccttcacaca tactcctcct ctggatccac aggaactgga tattctgaaa 240
accgtaaagg aaatcacagg gtttttgctg attcaggctt ggcctgaaaa caggacggac 300
ctccatgcct ttgagaacct agaaatcata cgcggcagga ccaagcaaca tggtcagttt 360
tctcttgcag tcgtcagcct gaacataaca tccttgggat tacgctccct caaggagata 420
agtgatggag atgtgataat ttcaggaaac aaaaatttgt gctatgcaaa tacaataaac 480
tggaaaaaac tgtttgggac ctccggtcag aaaaccaaaa ttataagcaa cagaggtgaa 540
aacagctgca aggccacagg ccaggtctgc catgccttgt gctcccccga gggctgctgg 600
ggcccggagc ccagggactg cgtctcttgc cggaatgtca gccgaggcag ggaatgcgtg 660
gacaagtgca accttctgga gggtgagcca agggagtttg tggagaactc tgagtgcata 720
cagtgccacc cagagtgcct gcctcaggcc atgaacatca cctgcacagg acggggacca 780
gacaactgta tccagtgtgc ccactacatt gacggccccc actgcgtcaa gacctgcccg 840
gcaggagtca tgggagaaaa caacaccctg gtctggaagt acgcagacgc cggccatgtg 900
tgccacctgt gccatccaaa ctgcacctac ggatgcactg ggccaggtct tgaaggctgt 960
ccaacgaatg ggcctaagat cccgtccatc gccactggga tggtgggggc cctcctcttg 1020
ctgctggtgg tggccctggg gatcggcctc ttcatg 1056

<210> SEQ ID NO 15
<211> LENGTH: 18
<212> TYPE: PRT
<213> ORGANISM: Artificial Sequence
<220> FEATURE:
<223> OTHER INFORMATION: T2A

<400> SEQUENCE: 15

Glu Gly Arg Gly Ser Leu Leu Thr Cys Gly Asp Val Glu Glu Asn Pro
1 5 10 15

Gly Pro

<210> SEQ ID NO 16
<211> LENGTH: 54
<212> TYPE: DNA
<213> ORGANISM: Artificial Sequence
<220> FEATURE:
<223> OTHER INFORMATION: T2A

<400> SEQUENCE: 16
gagggcaggg gaagtcttct aacatgcggg gacgtggagg aaaatcccgg cccc 54

<210> SEQ ID NO 17

<211> LENGTH: 2880
<212> TYPE: DNA
<213> ORGANISM: Artificial Sequence
<220> FEATURE:
<223> OTHER INFORMATION: chimeric antigen receptor cassette

<400> SEQUENCE: 17
gagtaattca tacaaaagga ctcgcccctg ccttggggaa tcccagggac cgtcgttaaa 60
ctcccactaa cgtagaaccc agagatcgct gcgttcccgc cccctcaccc gcccgctctc 120
gtcatcactg aggtggagaa gagcatgcgt gaggctccgg tgcccgtcag tgggcagagc 180
gcacatcgcc cacagtcccc gagaagttgg ggggaggggt cggcaattga accggtgcct 240
agagaaggtg gcgcggggta aactgggaaa gtgatgtcgt gtactggctc cgcctttttc 300
ccgagggtgg gggagaaccg tatataagtg cagtagtcgc cgtgaacgtt ctttttcgca 360
acgggtttgc cgccagaaca caggtaagtg ccgtgtgtgg ttcccgcggg cctggcctct 420
ttacgggtta tggcccttgc gtgccttgaa ttacttccac gcccctggct gcagtacgtg 480
attcttgatc ccgagcttcg ggttggaagt gggtgggaga gttcgaggcc ttgcgcttaa 540
ggagcccctt cgcctcgtgc ttgagttgag gcctggcttg ggcgctgggg ccgccgcgtg 600
cgaatctggt ggcaccttcg cgcctgtctc gctgctttcg ataagtctct agccatttaa 660
aatttttgat gacctgctgc gacgcttttt ttctggcaag atagtcttgt aaatgcgggc 720
caagatctgc acactggtat ttcggttttt ggggccgcgg gcggcgacgg ggcccgtgcg 780
tcccagcgca catgttcggc gaggcggggc ctgcgagcgc ggccaccgag aatcggacgg 840
gggtagtctc aagctggccg gcctgctctg gtgcctggcc tcgcgccgcc gtgtatcgcc 900
ccgccctggg cggcaaggct ggcccggtcg gcaccagttg cgtgagcgga aagatggccg 960
cttcccggcc ctgctgcagg gagctcaaaa tggaggacgc ggcgctcggg agagcgggcg 1020
ggtgagtcac ccacacaaag gaaaagggcc tttccgtcct cagccgtcgc ttcatgtgac 1080
tccacggagt accgggcgcc gtccaggcac ctcgattagt tctcgagctt ttggagtacg 1140
tcgtctttag gttgggggga ggggttttat gcgatggagt ttccccacac tgagtgggtg 1200
gagactgaag ttaggccagc ttggcacttg atgtaattct ccttggaatt tgcccttttt 1260
gagtttggat cttggttcat tctcaagcct cagacagtgg ttcaaagttt ttttcttcca 1320
tttcaggtgt cgtgattcga attcgccgcc accatggcct taccagtgac cgccttgctc 1380
ctgccgctgg ccttgctgct ccacgccgcc aggccggaca tcgtgctgac acagagccct 1440
gcttctctgg ccgtgtctct tggacagagg gccaccatgt cttgtagagc cggcgagagc 1500
gtggacatct tcggcgtggg atttctgcac tggtatcagc agaagcccgg ccagcctcct 1560
aagctgctga tctacagagc cagcaacctg gaaagcggca tccctgtgcg gtttagcggc 1620
acaggcagca gaaccgactt caccctgatc atcgaccccg tggaagccga tgatgtggcc 1680
acctactact gccagcagac caacgaggac ccctacacat ttggcggagg caccaagctg 1740
gaaatcaagg gtggaggtgg cagcggagga ggtgggtccg gcggtggagg aagcgaggtt 1800
cagctgcagc agtctggcgc tgaactggtt gaacctggcg cctctgtgaa gctgagctgt 1860
accgccagcg gcttcaacat caaggacacc tacatgcact gggtcaagca gaggcctgag 1920
cagggactcg agtggatcgg cagaatcgat cccgccaacg gcaacagcaa atacgtgccc 1980
aagttccagg gcaaagccac catcaccgcc gacacctcta gcaacacagc ctacctgcag 2040
ctcaccagcc tgacctctga agataccgcc gtgtactact gcgccccttt cggctactac 2100
gtgtccgatt acgccatggc ctattggggc cagggcacaa gcgtgacagt cagctctacc 2160
acgacgccag cgccgcgacc accaacaccg gcgcccacca tcgcgtcgca gcccctgtcc 2220
ctgcgcccag aggcgtgccg gccagcggcg gggggcgcag tgcacacgag ggggctggac 2280
ttcgcctgtg atatctacat ttgggcccct ctggctggta cttgcggggt cctgctgctt 2340
tcactcgtga tcactcttta ctgtaagcgc ggtcggaaga agctgctgta catctttaag 2400
caacccttca tgaggcctgt gcagactact caagaggagg acggctgttc atgccggttc 2460
ccagaggagg aggaaggcgg ctgcgaactg agagtgaagt tcagcaggag cgcagacgcc 2520
cccgcgtaca agcagggcca gaaccagctc tataacgagc tcaatctagg acgaagagag 2580
gagtacgatg ttttggacaa gagacgtggc cgggaccctg agatgggggg aaagccgaga 2640
aggaagaacc ctcaggaagg cctgtacaat gaactgcaga aagataagat ggcggaggcc 2700
tacagtgaga ttgggatgaa aggcgagcgc cggaggggca aggggcacga tggcctttac 2760
cagggtctca gtacagccac caaggacacc tacgacgccc ttcacatgca ggccctgccc 2820
cctcgcgagg gcaggggaag tcttctaaca tgcggggacg tggaggaaaa tcccggcccc 2880

<210> SEQ ID NO 18
<211> LENGTH: 3939
<212> TYPE: DNA
<213> ORGANISM: Artificial Sequence
<220> FEATURE:
<223> OTHER INFORMATION: chimeric antigen receptor cassette

<400> SEQUENCE: 18
gagtaattca tacaaaagga ctcgcccctg ccttggggaa tcccagggac cgtcgttaaa 60
ctcccactaa cgtagaaccc agagatcgct gcgttcccgc cccctcaccc gcccgctctc 120
gtcatcactg aggtggagaa gagcatgcgt gaggctccgg tgcccgtcag tgggcagagc 180
gcacatcgcc cacagtcccc gagaagttgg ggggaggggt cggcaattga accggtgcct 240
agagaaggtg gcgcggggta aactgggaaa gtgatgtcgt gtactggctc cgcctttttc 300
ccgagggtgg gggagaaccg tatataagtg cagtagtcgc cgtgaacgtt ctttttcgca 360
acgggtttgc cgccagaaca caggtaagtg ccgtgtgtgg ttcccgcggg cctggcctct 420
ttacgggtta tggcccttgc gtgccttgaa ttacttccac gcccctggct gcagtacgtg 480
attcttgatc ccgagcttcg ggttggaagt gggtgggaga gttcgaggcc ttgcgcttaa 540
ggagcccctt cgcctcgtgc ttgagttgag gcctggcttg ggcgctgggg ccgccgcgtg 600
cgaatctggt ggcaccttcg cgcctgtctc gctgctttcg ataagtctct agccatttaa 660
aatttttgat gacctgctgc gacgcttttt ttctggcaag atagtcttgt aaatgcgggc 720
caagatctgc acactggtat ttcggttttt ggggccgcgg gcggcgacgg ggcccgtgcg 780
tcccagcgca catgttcggc gaggcggggc ctgcgagcgc ggccaccgag aatcggacgg 840
gggtagtctc aagctggccg gcctgctctg gtgcctggcc tcgcgccgcc gtgtatcgcc 900
ccgccctggg cggcaaggct ggcccggtcg gcaccagttg cgtgagcgga aagatggccg 960
cttcccggcc ctgctgcagg gagctcaaaa tggaggacgc ggcgctcggg agagcgggcg 1020
ggtgagtcac ccacacaaag gaaaagggcc tttccgtcct cagccgtcgc ttcatgtgac 1080
tccacggagt accgggcgcc gtccaggcac ctcgattagt tctcgagctt ttggagtacg 1140
tcgtctttag gttgggggga ggggttttat gcgatggagt ttccccacac tgagtgggtg 1200
gagactgaag ttaggccagc ttggcacttg atgtaattct ccttggaatt tgcccttttt 1260
gagtttggat cttggttcat tctcaagcct cagacagtgg ttcaaagttt ttttcttcca 1320

-continued

```
tttcaggtgt cgtgattcga attcgccgcc accatggcct taccagtgac cgccttgctc   1380
ctgccgctgg ccttgctgct ccacgccgcc aggccggaca tcgtgctgac acagagccct   1440
gcttctctgg ccgtgtctct tggacagagg gccaccatgt cttgtagagc cggcgagagc   1500
gtggacatct tcggcgtggg atttctgcac tggtatcagc agaagcccgg ccagcctcct   1560
aagctgctga tctacagagc cagcaacctg gaaagcggca tccctgtgcg gtttagcggc   1620
acaggcagca gaaccgactt caccctgatc atcgaccccg tggaagccga tgatgtggcc   1680
acctactact gccagcagac caacgaggac ccctacacat ttggcggagg caccaagctg   1740
gaaatcaagg gtggaggtgg cagcggagga ggtgggtccg gcggtggagg aagcgaggtt   1800
cagctgcagc agtctggcgc tgaactggtt gaacctggcg cctctgtgaa gctgagctgt   1860
accgccagcg gcttcaacat caaggacacc tacatgcact gggtcaagca gaggcctgag   1920
cagggactcg agtggatcgg cagaatcgat cccgccaacg gcaacagcaa atacgtgccc   1980
aagttccagg gcaaagccac catcaccgcc gacacctcta gcaacacagc ctacctgcag   2040
ctcaccagcc tgacctctga agataccgcc gtgtactact gcgccccttt cggctactac   2100
gtgtccgatt acgccatggc ctattggggc cagggcacaa gcgtgacagt cagctctacc   2160
acgacgccag cgccgcgacc accaacaccg gcgcccacca tcgcgtcgca gcccctgtcc   2220
ctgcgcccag aggcgtgccg gccagcggcg gggggcgcag tgcacacgag ggggctggac   2280
ttcgcctgtg atatctacat ttgggcccct ctggctggta cttgcggggt cctgctgctt   2340
tcactcgtga tcactcttta ctgtaagcgc ggtcggaaga agctgctgta catctttaag   2400
caacccttca tgaggcctgt gcagactact caagaggagg acggctgttc atgccggttc   2460
ccagaggagg aggaaggcgg ctgcgaactg agagtgaagt tcagcaggag cgcagacgcc   2520
cccgcgtaca agcagggcca gaaccagctc tataacgagc tcaatctagg acgaagagag   2580
gagtacgatg ttttggacaa gagacgtggc cgggaccctg agatgggggg aaagccgaga   2640
aggaagaacc ctcaggaagg cctgtacaat gaactgcaga aagataagat ggcggaggcc   2700
tacagtgaga ttgggatgaa aggcgagcgc cggaggggca aggggcacga tggcctttac   2760
cagggtctca gtacagccac caaggacacc tacgacgccc ttcacatgca ggccctgccc   2820
cctcgcgagg gcaggggaag tcttctaaca tgcggggacg tggaggaaaa tcccggcccc   2880
atgtggctgc agagcctgct gctcttgggc actgtggcct gcagcatctc tcgcaaagtg   2940
tgtaacggaa taggtattgg tgaatttaaa gactcactct ccataaatgc tacgaatatt   3000
aaacacttca aaaactgcac ctccatcagt ggcgatctcc acatcctgcc ggtggcattt   3060
aggggtgact ccttcacaca tactcctcct ctggatccac aggaactgga tattctgaaa   3120
accgtaaagg aaatcacagg gtttttgctg attcaggctt ggcctgaaaa caggacggac   3180
ctccatgcct ttgagaacct agaaatcata cgcggcagga ccaagcaaca tggtcagttt   3240
tctcttgcag tcgtcagcct gaacataaca tccttgggat tacgctccct caaggagata   3300
agtgatggag atgtgataat ttcaggaaac aaaaatttgt gctatgcaaa tacaataaac   3360
tggaaaaaac tgtttgggac ctccggtcag aaaaccaaaa ttataagcaa cagaggtgaa   3420
aacagctgca aggccacagg ccaggtctgc catgccttgt gctcccccga gggctgctgg   3480
ggcccggagc ccagggactg cgtctcttgc cggaatgtca gccgaggcag ggaatgcgtg   3540
gacaagtgca accttctgga gggtgagcca agggagtttg tggagaactc tgagtgcata   3600
cagtgccacc cagagtgcct gcctcaggcc atgaacatca cctgcacagg acggggacca   3660
gacaactgta tccagtgtgc ccactacatt gacggccccc actgcgtcaa gacctgcccg   3720
```

```
gcaggagtca tgggagaaaa caacaccctg gtctggaagt acgcagacgc cggccatgtg   3780

tgccacctgt gccatccaaa ctgcacctac ggatgcactg ggccaggtct tgaaggctgt   3840

ccaacgaatg ggcctaagat cccgtccatc gccactggga tggtgggggc cctcctcttg   3900

ctgctggtgg tggccctggg gatcggcctc ttcatgtaa                           3939


<210> SEQ ID NO 19
<211> LENGTH: 840
<212> TYPE: PRT
<213> ORGANISM: Artificial Sequence
<220> FEATURE:
<223> OTHER INFORMATION: synthetic sequence

<400> SEQUENCE: 19

Asp Ile Val Leu Thr Gln Ser Pro Ala Ser Leu Ala Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Thr Gly Ser Arg Thr Asp Phe Thr Leu Ile Ile Asp
65                  70                  75                  80

Pro Val Glu Ala Asp Asp Val Ala Thr Tyr Tyr Cys Gln Gln Thr Asn
                85                  90                  95

Glu Asp Pro Tyr Thr Phe Gly Gly Gly Thr Lys Leu Glu Ile Lys Gly
            100                 105                 110

Gly Gly Gly Ser Gly Gly Gly Gly Ser Gly Gly Gly Gly Ser Glu Val
        115                 120                 125

Gln Leu Gln Gln Ser Gly Ala Glu Leu Val Glu Pro Gly Ala Ser Val
    130                 135                 140

Lys Leu Ser Cys Thr Ala Ser Gly Phe Asn Ile Lys Asp Thr Tyr Met
145                 150                 155                 160

His Trp Val Lys Gln Arg Pro Glu Gln Gly Leu Glu Trp Ile Gly Arg
                165                 170                 175

Ile Asp Pro Ala Asn Gly Asn Ser Lys Tyr Val Pro Lys Phe Gln Gly
            180                 185                 190

Lys Ala Thr Ile Thr Ala Asp Thr Ser Ser Asn Thr Ala Tyr Leu Gln
        195                 200                 205

Leu Thr Ser Leu Thr Ser Glu Asp Thr Ala Val Tyr Tyr Cys Ala Pro
    210                 215                 220

Phe Gly Tyr Tyr Val Ser Asp Tyr Ala Met Ala Tyr Trp Gly Gln Gly
225                 230                 235                 240

Thr Ser Val Thr Val Ser Ser Thr Thr Thr Pro Ala Pro Arg Pro Pro
                245                 250                 255

Thr Pro Ala Pro Thr Ile Ala Ser Gln Pro Leu Ser Leu Arg Pro Glu
            260                 265                 270

Ala Cys Arg Pro Ala Ala Gly Gly Ala Val His Thr Arg Gly Leu Asp
        275                 280                 285

Phe Ala Cys Asp Ile Tyr Ile Trp Ala Pro Leu Ala Gly Thr Cys Gly
    290                 295                 300

Val Leu Leu Leu Ser Leu Val Ile Thr Leu Tyr Cys Lys Arg Gly Arg
305                 310                 315                 320
```

-continued

```
Lys Lys Leu Leu Tyr Ile Phe Lys Gln Pro Phe Met Arg Pro Val Gln
                325                 330                 335

Thr Thr Gln Glu Glu Asp Gly Cys Ser Cys Arg Phe Pro Glu Glu Glu
            340                 345                 350

Glu Gly Gly Cys Glu Leu Arg Val Lys Phe Ser Arg Ser Ala Asp Ala
        355                 360                 365

Pro Ala Tyr Lys Gln Gly Gln Asn Gln Leu Tyr Asn Glu Leu Asn Leu
    370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg Glu Gly Arg Gly Ser Leu Leu Thr Cys Gly
465                 470                 475                 480

Asp Val Glu Glu Asn Pro Gly Pro Met Trp Leu Gln Ser Leu Leu Leu
                485                 490                 495

Leu Gly Thr Val Ala Cys Ser Ile Ser Arg Lys Val Cys Asn Gly Ile
            500                 505                 510

Gly Ile Gly Glu Phe Lys Asp Ser Leu Ser Ile Asn Ala Thr Asn Ile
        515                 520                 525

Lys His Phe Lys Asn Cys Thr Ser Ile Ser Gly Asp Leu His Ile Leu
    530                 535                 540

Pro Val Ala Phe Arg Gly Asp Ser Phe Thr His Thr Pro Pro Leu Asp
545                 550                 555                 560

Pro Gln Glu Leu Asp Ile Leu Lys Thr Val Lys Glu Ile Thr Gly Phe
                565                 570                 575

Leu Leu Ile Gln Ala Trp Pro Glu Asn Arg Thr Asp Leu His Ala Phe
            580                 585                 590

Glu Asn Leu Glu Ile Ile Arg Gly Arg Thr Lys Gln His Gly Gln Phe
        595                 600                 605

Ser Leu Ala Val Val Ser Leu Asn Ile Thr Ser Leu Gly Leu Arg Ser
    610                 615                 620

Leu Lys Glu Ile Ser Asp Gly Asp Val Ile Ile Ser Gly Asn Lys Asn
625                 630                 635                 640

Leu Cys Tyr Ala Asn Thr Ile Asn Trp Lys Lys Leu Phe Gly Thr Ser
                645                 650                 655

Gly Gln Lys Thr Lys Ile Ile Ser Asn Arg Gly Glu Asn Ser Cys Lys
            660                 665                 670

Ala Thr Gly Gln Val Cys His Ala Leu Cys Ser Pro Glu Gly Cys Trp
        675                 680                 685

Gly Pro Glu Pro Arg Asp Cys Val Ser Cys Arg Asn Val Ser Arg Gly
    690                 695                 700

Arg Glu Cys Val Asp Lys Cys Asn Leu Leu Glu Gly Glu Pro Arg Glu
705                 710                 715                 720

Phe Val Glu Asn Ser Glu Cys Ile Gln Cys His Pro Glu Cys Leu Pro
                725                 730                 735

Gln Ala Met Asn Ile Thr Cys Thr Gly Arg Gly Pro Asp Asn Cys Ile
```

```
            740                 745                 750

Gln Cys Ala His Tyr Ile Asp Gly Pro His Cys Val Lys Thr Cys Pro
        755                 760                 765

Ala Gly Val Met Gly Glu Asn Asn Thr Leu Val Trp Lys Tyr Ala Asp
    770                 775                 780

Ala Gly His Val Cys His Leu Cys His Pro Asn Cys Thr Tyr Gly Cys
785                 790                 795                 800

Thr Gly Pro Gly Leu Glu Gly Cys Pro Thr Asn Gly Pro Lys Ile Pro
                805                 810                 815

Ser Ile Ala Thr Gly Met Val Gly Ala Leu Leu Leu Leu Leu Val Val
            820                 825                 830

Ala Leu Gly Ile Gly Leu Phe Met
        835                 840


<210> SEQ ID NO 20
<211> LENGTH: 861
<212> TYPE: PRT
<213> ORGANISM: Artificial Sequence
<220> FEATURE:
<223> OTHER INFORMATION: synthetic sequence

<400> SEQUENCE: 20

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ser Leu
            20                  25                  30

Ala Val Ser Leu Gly Gln Arg Ala Thr Met Ser Cys Arg Ala Gly Glu
        35                  40                  45

Ser Val Asp Ile Phe Gly Val Gly Phe Leu His Trp Tyr Gln Gln Lys
    50                  55                  60

Pro Gly Gln Pro Pro Lys Leu Leu Ile Tyr Arg Ala Ser Asn Leu Glu
65                  70                  75                  80

Ser Gly Ile Pro Val Arg Phe Ser Gly Thr Gly Ser Arg Thr Asp Phe
                85                  90                  95

Thr Leu Ile Ile Asp Pro Val Glu Ala Asp Asp Val Ala Thr Tyr Tyr
            100                 105                 110

Cys Gln Gln Thr Asn Glu Asp Pro Tyr Thr Phe Gly Gly Gly Thr Lys
        115                 120                 125

Leu Glu Ile Lys Gly Gly Gly Gly Ser Gly Gly Gly Gly Ser Gly Gly
    130                 135                 140

Gly Gly Ser Glu Val Gln Leu Gln Gln Ser Gly Ala Glu Leu Val Glu
145                 150                 155                 160

Pro Gly Ala Ser Val Lys Leu Ser Cys Thr Ala Ser Gly Phe Asn Ile
                165                 170                 175

Lys Asp Thr Tyr Met His Trp Val Lys Gln Arg Pro Glu Gln Gly Leu
            180                 185                 190

Glu Trp Ile Gly Arg Ile Asp Pro Ala Asn Gly Asn Ser Lys Tyr Val
        195                 200                 205

Pro Lys Phe Gln Gly Lys Ala Thr Ile Thr Ala Asp Thr Ser Ser Asn
    210                 215                 220

Thr Ala Tyr Leu Gln Leu Thr Ser Leu Thr Ser Glu Asp Thr Ala Val
225                 230                 235                 240

Tyr Tyr Cys Ala Pro Phe Gly Tyr Tyr Val Ser Asp Tyr Ala Met Ala
                245                 250                 255

Tyr Trp Gly Gln Gly Thr Ser Val Thr Val Ser Ser Thr Thr Thr Pro
```

```
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Glu Gly Arg Gly Ser
                485                 490                 495

Leu Leu Thr Cys Gly Asp Val Glu Glu Asn Pro Gly Pro Met Trp Leu
            500                 505                 510

Gln Ser Leu Leu Leu Leu Gly Thr Val Ala Cys Ser Ile Ser Arg Lys
        515                 520                 525

Val Cys Asn Gly Ile Gly Ile Gly Glu Phe Lys Asp Ser Leu Ser Ile
    530                 535                 540

Asn Ala Thr Asn Ile Lys His Phe Lys Asn Cys Thr Ser Ile Ser Gly
545                 550                 555                 560

Asp Leu His Ile Leu Pro Val Ala Phe Arg Gly Asp Ser Phe Thr His
                565                 570                 575

Thr Pro Pro Leu Asp Pro Gln Glu Leu Asp Ile Leu Lys Thr Val Lys
            580                 585                 590

Glu Ile Thr Gly Phe Leu Leu Ile Gln Ala Trp Pro Glu Asn Arg Thr
        595                 600                 605

Asp Leu His Ala Phe Glu Asn Leu Glu Ile Ile Arg Gly Arg Thr Lys
    610                 615                 620

Gln His Gly Gln Phe Ser Leu Ala Val Val Ser Leu Asn Ile Thr Ser
625                 630                 635                 640

Leu Gly Leu Arg Ser Leu Lys Glu Ile Ser Asp Gly Asp Val Ile Ile
                645                 650                 655

Ser Gly Asn Lys Asn Leu Cys Tyr Ala Asn Thr Ile Asn Trp Lys Lys
            660                 665                 670

Leu Phe Gly Thr Ser Gly Gln Lys Thr Lys Ile Ile Ser Asn Arg Gly
        675                 680                 685
```

-continued

```
Glu Asn Ser Cys Lys Ala Thr Gly Gln Val Cys His Ala Leu Cys Ser
    690                 695                 700

Pro Glu Gly Cys Trp Gly Pro Glu Pro Arg Asp Cys Val Ser Cys Arg
705                 710                 715                 720

Asn Val Ser Arg Gly Arg Glu Cys Val Asp Lys Cys Asn Leu Leu Glu
                725                 730                 735

Gly Glu Pro Arg Glu Phe Val Glu Asn Ser Glu Cys Ile Gln Cys His
            740                 745                 750

Pro Glu Cys Leu Pro Gln Ala Met Asn Ile Thr Cys Thr Gly Arg Gly
        755                 760                 765

Pro Asp Asn Cys Ile Gln Cys Ala His Tyr Ile Asp Gly Pro His Cys
    770                 775                 780

Val Lys Thr Cys Pro Ala Gly Val Met Gly Glu Asn Asn Thr Leu Val
785                 790                 795                 800

Trp Lys Tyr Ala Asp Ala Gly His Val Cys His Leu Cys His Pro Asn
                805                 810                 815

Cys Thr Tyr Gly Cys Thr Gly Pro Gly Leu Glu Gly Cys Pro Thr Asn
            820                 825                 830

Gly Pro Lys Ile Pro Ser Ile Ala Thr Gly Met Val Gly Ala Leu Leu
        835                 840                 845

Leu Leu Leu Val Val Ala Leu Gly Ile Gly Leu Phe Met
    850                 855                 860
```

CHIMERIC ANTIGEN RECEPTOR FOR TREATMENT OF CANCER

This Application is a National Stage of International Application No. PCT/KR2021/005721 filed May 7, 2021, claiming priority based on Korean Patent Application No. 10-2020-0055248 filed May 8, 2020, the entire disclosures of which are incorporated herein by reference.

TECHNICAL FIELD

The present invention relates to a novel chimeric antigen receptor and the use thereof for treatment of cancer.

BACKGROUND ART

T cells expressing a chimeric antigen receptor (hereinafter also abbreviated as "CAR") refer to genetically engineered T cells obtained by introducing into T cells a gene encoding a receptor, which recognizes a cancer cell surface antigen expressed specifically on the surfaces of cancer cells, so as to be capable of killing the cancer cells. These T cells are also abbreviated herein as "CAR T-cells". Dr. Zelig Eshhar (who is both a chemist and an immunologist) and colleagues at the Weizmann Institute of Science in Israel found that, when T cells having a receptor that binds to an antigen expressed specifically on cancer cells are artificially generated, these T cells can kill cancer cells by targeting only the cancer cells and triggering an immune response. Based on this finding, they succeeded in generating T cells having a chimeric antigen receptor and reported these T cells in PNAS in 1989.

However, CAR T-cells generated in the early stage, i.e. the first-generation CAR T-cells contained only CD3ζ as a signaling domain, and had disadvantages in that the therapeutic effect thereof is insufficient and the duration time thereof is also short. Accordingly, efforts were made to improve the reactivity of CAR T-cells, and second-generation CAR T-cells containing a combination of CD3ζ and a costimulatory domain (CD28 or CD137/4-1BB) were generated and the number of these CAR T-cells remaining in vivo significantly increased compared to the number of the first-generation CAR T-cells. Meanwhile, the second-generation CAR T-cells contained one costimulatory domain, and CAR T-cells containing two costimulatory domains are referred to as third-generation CAR T-cells. Current studies are focused on the second-generation and third-generation CAR T-cells.

Regarding a method of treating cancer using CAR T-cells, there was a report that, when cytotoxic T cells modified to recognize CD19 were injected into three patients with end-stage chronic lymphoid leukemia (CCL), the leukemia was completely cured in two of the patients, and the condition lasted about 10 months (N. Engl J Med 2011; 365: 725-733 Aug. 25, 2011, Sic. Transl. Med 2011 Aug. 10; 3(95):95ra73). The CAR T-cells used in the report correspond to the second-generation CAR T-cells containing 4-1BB as a costimulatory domain and CD3ζ as a signaling domain. The antigen-binding domain of the CAR T-cell recognizes CD19 found on the surfaces of leukemia cancer cells as an antigen.

In addition, there was a report that, when 30 acute leukemia patients were treated by administering CTL019, 27 out of the patients experienced complete remission, 67% of all the patients experienced complete remission for 2 years, and 78% of the patients survived for 2 years (N Engl J Med 2014; 371:1507-1517, Oct. 16, 2014). This is quite surprising given that the patients were relapsed or refractory patients.

Currently, for treatment with various CAR T-cells, clinical trials are in progress for various cancers such as lymphoma and myeloma, and CAR T-cells as available pharmaceuticals are expected to appear in the market. Although CAR T-cells are not mass-produced products because they are autologous, but treatment of cancer with CAR T-cells is patient-tailored and the therapeutic effect thereof is so high that it cannot be compared with existing anticancer drugs.

Meanwhile, carcinoembryonic antigen (CEA) is a glycoprotein discovered in 1965 as an antigenic substance commonly present in colon cancer and fetal colonic mucosa. Since this CEA is widely expressed in various organ-derived cancers such as colorectal cancer, digestive cancer, pancreatic cancer, and lung cancer, it is also used as a marker for blood-based tumor marker tests. In the treatment of cancer with CAR T-cells, CAR T-cells can be applied to various cancers depending on the antigen targeted by the CAR-T cells to be used, but there is currently no development of CAR-T cell therapeutics targeting CEA.

DISCLOSURE

Technical Problem

An object of the present invention is to provide a novel chimeric antigen receptor targeting cancer cells, particularly cancer cells expressing carcinoembryonic antigen (CEA).

Another object of the present invention is to provide an immune cell expressing a chimeric antigen receptor according to the present invention, which may be used for the prevention or treatment of cancer, particularly cancer expressing carcinoembryonic antigen (CEA).

Still another object of the present invention is to provide a pharmaceutical composition for preventing or treating cancer, particularly cancer expressing carcinoembryonic antigen (CEA), using the immune cells according to the present invention.

Other objects and advantages of the present invention will become more apparent from the following detailed description of the invention, the appended claims and the accompanying drawings.

Technical Solution

One embodiment of the present invention is directed to a chimeric antigen receptor comprising a carcinoembryonic antigen (CEA)-binding domain.

In the present invention, the carcinoembryonic antigen-binding domain may comprise a VH domain set forth in SEQ ID NO: 1 and a VL domain set forth in SEQ ID NO: 2.

In the present invention, the carcinoembryonic antigen binding domain may comprise a flexible linker.

In the present invention, the flexible linker may be set forth in SEQ ID NO: 3.

The chimeric antigen receptor of the present invention may further comprise at least one of a hinge region and a signaling domain.

In the present invention, the hinge region may comprise CD8, CD28, 4-1BB, OX40, all or part of CD3 zeta (0 chain, T-cell receptor a or 3 chain, CD28, CD3E, CD45, CD4, CD5, CD8, CD9, CD16, CD22, CD33, CD37, CD64, CD80, CD86, CD134, CD137, ICOS, CD154, or combinations thereof.

In the present invention, the hinge region may be set forth in SEQ ID NO: 4.

In the present invention, the signaling domain may further comprise a transmembrane domain.

In the present invention, the transmembrane domain may comprise may be T cell receptor α or βchain, all or part of CD3 zeta (0 chain, CD28, CD3E, CD45, CD4, CDS, CD8, CD9, CD16, CD22, CD33, CD37, CD64, CD80, CD86, CD134, CD137, ICOS, CD154, or combinations thereof.

In the present invention, the transmembrane domain may be set forth in SEQ ID NO: 5.

In the present invention, the signaling domain may further comprise a costimulatory domain.

In the present invention, the costimulatory domain may comprise a ligand that binds to 4-1BB (CD137), OX40, CD27, CD28, CD30, CD40, PD-1, CD2, CD7, CD258, natural killing group 2 member C (NKG2C), natural killing group 2 member D (NKG2D), B7-H3, CD83, ICAM-1, LFA-1 (CD11a/CD18), ICOS, or combinations thereof.

In the present invention, the costimulatory domain may be set forth in SEQ ID NO: 6.

In the present invention, the signaling domain may comprise all or part of CD3 zeta (ζ), common FcR gamma (FcER1G), Fc gamma RIIIa, FcR beta (Fc epsilon Rib), CD3 gamma, CD3 delta, CD3 epsilon, CD79a, CD79b, DNAX-activating protein 10 (DAP10), DNAX-activating protein 12 (DAP12), or combinations thereof.

In the present invention, the signaling domain may be set forth in SEQ ID NO: 7.

In the present invention, the chimeric antigen receptor may further comprise a signal peptide.

In the present invention, the signal peptide may be set forth in SEQ ID NO: 8.

In the present invention, the chimeric antigen receptor may comprise a polypeptide set forth in SEQ ID NO: 9 or 10.

Another embodiment of the present invention is directed to a polynucleotide encoding the chimeric antigen receptor provided in the present invention.

In the present invention, the polynucleotide may be set forth in SEQ ID NO: 11 or 12.

Still another embodiment of the present invention is directed to an expression cassette comprising the polynucleotide provided in the present invention.

In the present invention, the expression cassette may further comprise a promoter.

In the present invention, the promoter may be an SFFV promoter, an elongation factor 1a (EF 1a) promoter, or a CAG promoter.

In the present invention, the expression cassette may further comprise a truncated EGFR gene (EGFRt) as an additional gene.

In the present invention, the polynucleotide and the truncated EGFR gene may be linked together by a cleavable linker.

In the present invention, the cleavable linker may be a T2A ribosomal skip element.

In the present invention, the expression cassette may comprise a polynucleotide set forth in SEQ ID NO: 17 or 18.

Yet another embodiment of the present invention is directed to a vector comprising the expression cassette provided in the present invention.

In the present invention, the vector may be a plasmid, transposon, cosmid or viral vector.

In the present invention, the vector may be a retroviral vector, an adenoviral vector, an adeno-associated virus (AAC) vector, a lentiviral vector, a poxvirus vector, a simian virus vector, a vaccinia virus vector or Sendai virus vector, an Epstein-Barr virus (EBV) vector, or an HSV vector.

Still yet another embodiment of the present invention is directed to a host cell transformed with the vector provided in the present invention.

In the present invention, the host cell may be a T cell or an NK cell.

In the present invention, a polypeptide that is expressed in the host cell may comprise a polypeptide set forth in SEQ ID NO: 19 or 20.

A further embodiment of the present invention is directed to a pharmaceutical composition for preventing or treating cancer, the pharmaceutical composition containing, as an active ingredient, the chimeric antigen receptor, polynucleotide, expression cassette, vector, host cell or polypeptide provided in the present invention.

In the present invention, the cancer may express carcinoembryonic antigen (CEA).

In the present invention, the cancer may be a solid cancer.

In the present invention, the cancer may be gastric cancer, liver cancer, glioblastoma, ovarian cancer, colorectal cancer, head and neck cancer, bladder cancer, renal cell cancer, breast cancer, metastatic cancer, prostate cancer, pancreatic cancer, bile duct cancer, melanoma, or lung cancer, preferably pancreatic cancer or biliary duct cancer, without being limited thereto.

Another further embodiment of the present invention is directed to a method for preventing or treating cancer, the method comprising a step of administering, to a subject, the chimeric antigen receptor, polynucleotide, expression cassette, vector, host cell, polypeptide expressed from the host cell, or pharmaceutical composition, provided in the present invention.

In the present invention, the cancer may express carcinoembryonic antigen (CEA).

In the present invention, the cancer may be a solid cancer.

In the present invention, the cancer may be gastric cancer, liver cancer, glioblastoma, ovarian cancer, colorectal cancer, head and neck cancer, bladder cancer, renal cell cancer, breast cancer, metastatic cancer, prostate cancer, pancreatic cancer, bile duct cancer, melanoma, or lung cancer, preferably pancreatic cancer or biliary tract cancer, without being limited thereto.

Advantageous Effects

The immune cells transformed to express the chimeric antigen receptor provided in the present invention may specifically recognize cancer cells, in particular, cancer cells expressing carcinoembryonic antigen (CEA), and induce death of the cancer cells, thereby effectively preventing or treating cancer.

BRIEF DESCRIPTION OF DRAWINGS

FIG. 1 schematically shows the structure of a chimeric antigen receptor according to an embodiment of the present invention.

FIG. 2 schematically shows the structure of a chimeric antigen receptor cassette according to an embodiment of the present invention.

FIG. 3 schematically shows the structure of a vector according to an embodiment of the present invention.

FIG. 4 shows the result of electrophoresis performed to confirm a constructed chimeric antigen receptor cassette inserted into a vector after restriction enzyme treatment in Example 1 of the present invention.

FIG. 5 shows the results of flow cytometry performed in Example 3 of the present invention in order to check whether CEA was expressed in various cancer cell lines.

FIG. 6 shows microscopic images of peripheral blood-derived T cells obtained by transforming Lenti-X 293 FT cells with a Lenti-anti-CEA-h(BBζ)-EGFRt-$2^{nd}$-CAR plasmid and then activating the cells, in Example 4 of the present invention.

FIG. 7 depicts images showing the results of fluorescence microscopy performed to observe whether HT29 cells expressed CEA, after immunofluorescence staining for CEA in Example 5 of the present invention.

FIG. 8 depicts images showing the results of fluorescence microscopy performed to observe a process in which anti-CEA CAR-T cells inserted with a chimeric antigen receptor cassette targeting CEA kill HT29 cells, in Example 5 of the present invention.

FIG. 9 is a graph showing the results of examining changes in cell death rate depending on the co-culture ratio of anti-CEA CAR T-cells inserted with a CEA-targeting chimeric antigen receptor cassette to a CEA-expressing HT29 cell line, in Example 5 of the present invention.

FIG. 10 is a graph showing the results of examining changes in cell death rate depending on the co-culture ratio of anti-CEA CAR T-cells inserted with a CEA-targeting chimeric antigen receptor cassette to a CEA-expressing Capan1 cell line, in Example 5 of the present invention.

BEST MODE

The chimeric antigen receptor according to an embodiment of the present invention may consist of or comprise a polypeptide set forth in SEQ ID NO: 9, which consists of a CEA binding domain-CD8 hinge-CD8 transmembrane domain-4-1BB-CD3ζ, or may consist of or comprise a polypeptide set forth in SEQ ID NO: 10, which consists of a signal peptide-CEA binding domain-CD8 hinge-CD8 transmembrane domain-4-1BB-CD3c, without being not limited thereto.

The chimeric antigen receptor according to an embodiment of the present invention may be used for prevention, alleviation or treatment of cancer, preferably cancer expressing carcinoembryonic antigen (CEA).

MODE FOR INVENTION

Unless defined otherwise herein, all technical and scientific terms used herein have the same meaning as commonly understood by one of ordinary skill in the art to which the present invention pertains. Although any methods and materials similar or equivalent to those described herein can be used for the testing or practice of the present invention, suitable methods and materials are described herein. In describing and claiming the present invention, the following terminology will be used in accordance with the definitions set forth below. It is also to be understood that the terminology used herein is for the purpose of describing particular embodiments only, and is not intended to be limiting. The articles "a" and "an" are used herein to refer to one or to more than one (i.e., to at least one) of the grammatical object of the article.

One embodiment of the present invention is directed to a chimeric antigen receptor comprising a carcinoembryonic antigen (CEA) binding domain.

As used herein, the term "chimeric antigen receptor" or "CAR" refers to an engineered receptor comprising an extracellular antigen binding domain and an intracellular signaling domain. While the most common type of CAR comprises a single-chain variable fragment (scFv) derived from a monoclonal antibody fused to a transmembrane and intracellular domain of a T cell co-receptor, such as the CD3ζ chain, the invention described herein is not limited to these domains. Rather, as used herein, "chimeric antigen receptor" or "CAR" refers to any receptor engineered to express any intracellular signaling molecule and an extracellular antigen binding domain fused or linked to any intracellular signaling molecule.

In the present invention, the binding domain may include a single-chain variable fragment (scFv) capable of specifically recognizing carcinoembryonic antigen (CEA).

As used herein, the term "single-chain variable fragment" or "scFv" refers to a fusion protein of the variable heavy (VH) and variable light (VL) chains of an antibody with a peptide linker between the VL and VH.

In the present invention, the carcinoembryonic antigen binding domain may comprise a VH domain set forth in SEQ ID NO: 1 and a VL domain set forth in SEQ ID NO: 2.

In addition, in the present invention, the VH domain and the VL domain may be linked together by a flexible linker. In the present invention, the flexible linker may be a glycine/serine linker of about 10 to 30 amino acids (e.g., 30, 25, 20, 19, 18, 17, 16, 15, 14, 13, 12, 11, 10, 9, 8, 7, 6 or 5 amino acids), preferably 15 amino acids in length. In the present invention, the length of the linker may be an important determinant of the chimeric antigen receptor. Thus, linkers having a shorter length than the lower limit of the above range enhance affinity but can also lead to intracellular multimer formation, thus impairing expression of the CAR. On the other hand, linkers having a longer length than the upper limit of the above range may decrease antigen affinity by moving the VL and VH CDRs further apart in space.

In the present invention, the flexible linker set forth in SEQ ID NO: 3 is preferable because it may increase the efficiency of binding to the target carcinoembryonic antigen.

The chimeric antigen receptor of the present invention may further comprise at least one of a hinge region (or spacer) and a signaling domain.

In the present invention, the hinge region is a portion connecting the antigen binding domain and the transmembrane domain, and is also called spacer. The hinge region has the purpose for expanding the antigen binding domain from T cell membrane or NK cell membrane.

In the present invention, the hinge sequence may be obtained, for example, from any suitable sequence from any genus, including human or a part thereof, or may include a hinge region of a human protein including CD8, CD28, 4-1BB, OX40, all or part of CD3 zeta (ζ) chain, T cell receptor α or β chain, CD28, CD36, CD45, CD4, CD5, CD8, CD9, CD16, CD22, CD33, CD37, CD64, CD80, CD86, CD134, CD137, ICOS, CD154, functional derivatives thereof, or combinations thereof, which are commonly used in the art, without being limited thereto.

In addition, in the present invention, the hinge region may comprise one selected from, but not limited to, immunoglobulin (e.g. IgG1, IgG2, IgG3, IgG4, and IgD).

In the present invention, the hinge region may be a CD8 hinge region set forth in SEQ ID NO: 4, without being limited thereto.

In the present invention, the signaling domain refers to the portion of the chimeric antigen receptor that is found or is engineered to be found inside a T cell. In the present invention, the signaling domain may or may not also contain a transmembrane domain which anchors the chimeric antigen receptor in the plasma membrane of a T cell.

In the present invention, the transmembrane domain and the signaling domain may be derived from the same protein (e.g., CD3ζ). Alternatively, the transmembrane domain and the signaling domain may be derived from different proteins (e.g., the transmembrane domain of a CD28 and the intracellular signaling domain of a CD3ζ molecule, or vice versa).

In the present invention, the transmembrane domain comprises a hydrophobic polypeptide that spans the cellular membrane. In particular, the transmembrane domain may span from one side of a cell membrane (extracellular) through the other side of the cell membrane (intracellular or cytoplasmic).

In the present invention, the transmembrane domain may be in the form of an alpha helix or a beta barrel, or combinations thereof. In addition, in the present invention, the transmembrane domain may comprise a polytopic protein, which has many transmembrane segments, each alpha-helical, beta sheets, or combinations thereof.

In the present invention, the transmembrane domain may comprise, for example, a T cell receptor α or β chain, all or part of CD3 zeta (0 chain, CD28, CD3E, CD45, CD4, CDS, CD8, CD9, CD16, CD22, CD33, CD37, CD64, CD80, CD86, CD134, CD137, ICOS, CD154, functional derivatives thereof, or combinations thereof, without being limited thereto.

In the present invention, the transmembrane domain may be, for example, a polypeptide comprising hydrophobic residues such as leucine and valine, which is artificially designed. In one embodiment of the present invention, a triplet of phenylalanine, tryptophan and valine is may be found at each end of the synthetic transmembrane domain.

In the present invention, the transmembrane domain may be a CD8 transmembrane domain set forth in SEQ ID NO: 5, without being limited thereto.

In the present invention, at least one costimulatory domain may be further included between the transmembrane domain and the signaling domain. In the present invention, the costimulatory domain is a portion through which a costimulatory signal is transmitted. The costimulatory domain may serve to help CAR-T cells or CAR-NK cells that recognize a specific antigen bound to the antigen-binding domain to self-proliferate while eliciting an immune response, and act to transmit a signal so as to increase the in vivo retention time of the cells.

In the present invention, the costimulatory domain may comprise a functional signaling domain derived from a polypeptide comprising a ligand that binds to 4-1BB (CD137), OX40, CD27, CD28, CD30, CD40, PD-1, CD2, CD7, CD258, natural killing group 2 member C (NKG2C), natural killing group 2 member D (NKG2D), B7-H3, CD83, ICAM-1, LFA-1 (CD11 a/CD18), or ICOS, active fragments thereof, functional derivatives thereof, or combinations thereof, without being limited thereto.

In the present invention, the costimulatory domain may be 4-1BB set forth in SEQ ID NO: 6, without being limited thereto.

In the present invention, the signaling domain may comprise a polypeptide that provides activation of an immune cell to stimulate or activate at least some aspect of the immune cell signaling pathway.

In the present invention, the signaling domain may comprise a functional signaling domain derived from a polypeptide comprising all or part of CD3 zeta (0, common FcR gamma (FcER1G), Fc gamma RIIIa, FcR beta (Fc epsilon Rib), CD3 gamma, CD3 delta, CD3 epsilon, CD79a, CD79b, DNAX-activating protein 10 (DAP10), DNAX-activating protein 12 (DAP12), active fragments thereof, functional derivatives thereof, or combinations thereof, without being limited thereto. Such signaling domains are known in the art.

In the present invention, the signaling domain may be CD3 zeta (0 set forth in SEQ ID NO: 7, without being limited thereto.

In addition, the chimeric antigen receptor of the present invention may further comprise a signal peptide.

In the present invention, the "signal peptide" may include a peptide sequence which is a peptide of any secreted or transmembrane protein that directs the transport of the chimeric antigen receptor of the present invention to the cell membrane and cell surface, and provides correct localization of the chimeric antigen receptor of the present invention. In particular, the signal peptide in the present invention directs the chimeric antigen receptor of the present invention to the cellular membrane, wherein the extracellular portion of the chimeric antigen receptor is displayed on the cell surface, the transmembrane portion spans the plasma membrane, and the active domain is in the cytoplasmic portion, or interior of the cell.

In the present invention, as the signal peptide, any peptide may be used without limitation as long as it has the above function. For example, the signal peptide may be an N-terminal CD8α signal peptide set forth in SEQ ID NO: 8.

Figures 1, 2:
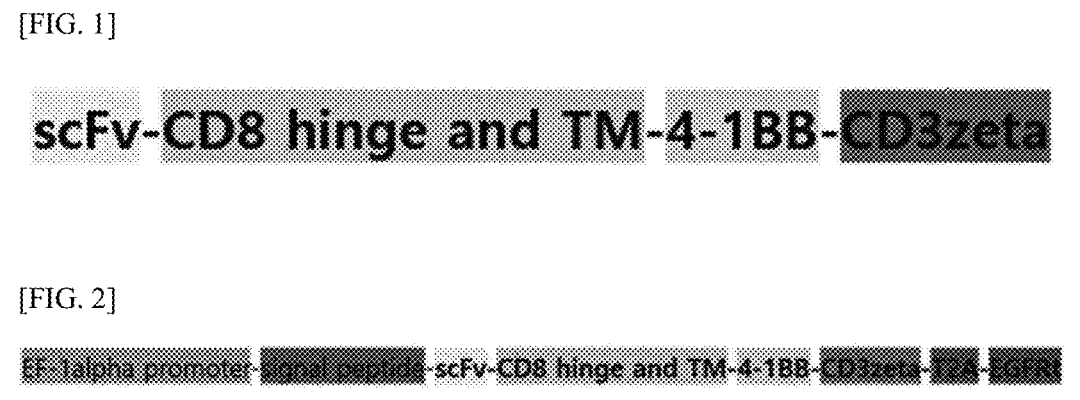

FIG. 1 schematically shows the structure of a chimeric antigen receptor according to an embodiment of the present invention. The chimeric antigen receptor may consist of or comprise a polypeptide set forth in SEQ ID NO: 9, which consists of or comprises a CEA binding domain-CD8 hinge-CD8 transmembrane domain-4-1BB-CD3ζ, or may consist of or comprise a polypeptide set forth in SEQ ID NO: 10, which consists of or comprises a signal peptide-CEA binding domain-CD8 hinge-CD8 transmembrane domain-4-1BB-CD3ζ.

Another embodiment of the present invention is directed to a polynucleotide encoding the chimeric antigen receptor according to the present invention.

In the present invention, the polynucleotide encoding the chimeric antigen receptor is easily produced from the amino acid sequence of the specified chimeric antigen receptor by any conventional method. A nucleotide sequence encoding the amino acid sequence can be obtained from the aforementioned NCBI RefSeq IDs or accession numbers of GenBenk for the amino acid sequence of each domain, and the nucleic acid of the present invention can be produced using a standard molecular biological and/or chemical procedure. For example, based on the nucleotide sequence, the polynucleotide can be synthesized, and the polynucleotide of the present invention can be produced by combining DNA fragments obtained from a cDNA library using a polymerase chain reaction (PCR).

The polynucleotide of the present invention may be part of a gene or an expression or cloning cassette, without being limited thereto.

As used herein, the term "polynucleotide" is defined as a chain of nucleotides. Polynucleotides include DNA and RNA. Furthermore, nucleic acids are polymers of nucleotides. Thus, the terms "nucleic acid" and "polynucleotide" as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein, the polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and polymerase chain reaction (PCR), and the like, and by synthetic means.

In the present invention, the polynucleotide encoding the chimeric antigen receptor set forth in SEQ ID NO: 9 may be set forth in SEQ ID NO: 11, and the polynucleotide encoding the chimeric antigen receptor set forth in SEQ ID NO: 10 may be set forth in SEQ ID NO: 12, without being limited thereto.

Still another embodiment of the present invention is directed to an expression cassette comprising the polynucleotide provided in the present invention.

The expression cassette of the present invention may contain expression control sequences capable of regulating expression of the polynucleotide of the present invention, such as a promoter, an enhancer, a polyadenylation signal, a transcription terminator or an internal ribosome entry site (IRES).

In the present invention, examples of the promoter include, but are not limited to, an SFFV promoter, an elongation factor 1a (EF 1a) promoter, or a CAG (chicken beta-actin promoter with a CMV enhancer) promoter.

The expression cassette of the present invention may further comprise a truncated EGFR gene (EGFRt) as an additional gene sequence useful for monitoring expression thereof. In the present invention, the EGFRt is a non-immunogenic selection tool. For example, the EGFRt may be used to select T cells or NK cells transformed with an EGFRt-containing cassette in immunomagnetic selection performed using biotinylated cetuximab and anti-biotin microbeads, and may also be used as a tracking marker in flow cytometry for T cell or NK cell tracking. In addition, the EGFRt is demonstrated to have suicide gene potential through cetuximab/Erbitux® mediated antibody dependent cellular cytotoxicity (ADCC) pathways.

In the present invention, the truncated EGFR gene (EGFRt) may consist of a gene encoding a polypeptide set forth in SEQ ID NO: 13, or may be set forth in SEQ ID NO: 14, without being limited thereto.

In addition, in the present invention, the truncated EGFR gene (EGFRt) and one end of the Fcγ receptor binding domain of the polynucleotide of the present invention may be linked together by a ribosomal skip element which is a cleavable linker.

As used herein, the term "ribosomal skip" refers to an alternative mechanism of translation in which a specific peptide prevents the ribosome of a cell from covalently linking a new inserted amino acid and instead allows it to continue translation thus resulting in a co-translational cleavage of the polyprotein. This process is induced by a "2A ribosomal skip" element or cis-acting hydrolase element (e.g., CHYSEL sequence). In some embodiments, this sequence comprises a non-conserved amino acid sequence with a strong alpha-helical propensity followed by the consensus sequence –D(V/I)ExNPG P, where x is any amino acid. Apparent cleavage occurs between G and P. In the present invention, the ribosomal skip element may be a 2A ribosomal skip element, preferably a 5' T2A ribosomal skip element, without being limited thereto.

In the present invention, the cleavable linker may consist of a gene encoding a polypeptide set forth in SEQ ID NO: 15, or may be set forth in SEQ ID NO: 16, without being limited thereto.

FIG. 2 schematically shows the structure of a chimeric antigen receptor cassette according to an embodiment of the present invention. The chimeric antigen receptor cassette may be consist of or comprise a polynucleotide set forth in SEQ ID NO: 17, which consists of a polynucleotide encoding EF-1α promoter-N-terminal CD8α signal peptide-CEA binding domain (scFv)-CD8 hinge-CD8 transmembrane domain (TM)-4-1BB-CD3ζ-T2A, or may consist of or comprise a polypeptide set forth in SEQ ID NO: 18, which consists of a polynucleotide encoding EF-1α promoter-N-terminal CD8α signal peptide-CEA binding domain (scFv)-CD8 hinge-CD8 transmembrane domain (TM)-4-1BB-CD3ζ-T2A-EGFRt, without being limited thereto.

Yet another embodiment of the present invention is directed to a vector comprising the expression cassette provided in the present invention.

The vector that is used in the present invention may be, for example, a plasmid, transposon, cosmid or viral vector (e.g., phage, retrovirus, lentivirus or adenovirus).

In the present invention, the vector may be a retroviral vector (including an oncoretrovirus vector, a lentiviral vector, and a pseudo-type vector), an adenoviral vector, an adeno-associated virus (AAC) vector, a lentiviral vector, a pox A viral vector, a simian virus vector, a vaccinia virus vector or Sendai virus vector, an Epstein-Barr virus (EBV) vector, or an HSV vector, without being limited thereto.

FIG. 3 schematically shows the structure of a vector according to an embodiment of the present invention. The vector may be designed to contain a polynucleotide comprising a polynucleotide set forth in SEQ ID NO: 18, which encodes EF-1α promoter-N-terminal CD8α signal peptide-CEA binding domain (scFv)-CD8 hinge-CD8 transmembrane domain (TM)-4-1BB-CD3ζ-T2A-EGFRt, without being limited thereto.

Still yet another embodiment of the present invention is directed to a host cell transformed with the vector provided in the present invention.

As used herein, the term "host cell" refers to any type of cell that can contain the expression vector. The host cell can be a eukaryotic cell (e.g., plant, animal, fungi, or algae), a prokaryotic cell (e.g., bacteria or protozoa) or a viral or retroviral vector. The host cell can be a cultured or "off-the-shelf" cell or a primary cell (i.e., isolated directly from a subject). The host cell can be an adherent cell or a suspended cell, i.e., a cell that grows in suspension. Suitable host cells are known in the art and include, for instance, DH5 a *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. In addition, in the present invention, for purposes of producing a recombinant CAR, the host cell can be a mammalian cell. Preferably, the host cell may be a human cell.

In the present invention, the host cell can be of any cell type, can originate from any type of tissue, and can be of any developmental stage. For example, a cell collected, isolated, purified or induced from a body fluid, a tissue or an organ such as blood (peripheral blood, umbilical cord blood, etc.) or bone marrow can be used.

The host cell that is used in the present invention may be an immune cell [a T cell, a dendritic cell, a B cell, a hematopoietic stem cell, a macrophage, a monocyte, a NK cell or a hematopoietic cell (a neutrophil, a basophil)], a peripheral blood mononuclear cell (PBMC), an umbilical cord blood mononuclear cell, a fibroblast, a precursor adipocyte, a hepatocyte, a skin keratinocyte, a mesenchymal stem cell, an adipose stem cell, or various cancer cell lines.

Preferably, the host cell may be a T cell or an NK cell, more preferably a CD4+, CD8+ T cell, an effector T cell, a memory T cell, or a regulatory T cell, without being limited thereto. Methods for selecting suitable mammalian host cells and methods for transformation, culture, amplification, screening, and purification of cells are known in the art.

A further embodiment of the present invention is directed to a polypeptide that is expressed from the transformed host cell provided in the present invention.

In the present invention, the polypeptide that is expressed from the host cell may consist of or comprise CEA binding domain (scFv)-CD8 hinge-CD8 transmembrane domain (TM)-4-1BB-CD3ζ-T2A-EGFRt set forth in SEQ ID NO: 19, or may consist of or comprise N-terminal CD8α signal peptide-CEA binding domain (scFv)-CD8 hinge-CD8 transmembrane domain (TM)-4-1BB-CD3ζ-T2A-EGFRt set forth in SEQ ID NO: 20.

Another further embodiment of the present invention is directed to a pharmaceutical composition for preventing or treating cancer, the pharmaceutical composition containing, as an active ingredient, the chimeric antigen receptor, polynucleotide, expression cassette, vector, host cell or polypeptide expressed from the host cell, provided in the present invention.

The host cell transformed to express the chimeric antigen receptor provided in the present invention can effectively prevent or treat cancer by specifically recognizing carcinoembryonic antigen (CEA) present in cancer cells and then killing the cancer cells.

As used herein, the term "cancer" refers to or describes the physiological condition in mammals that is typically characterized by unregulated cell growth. In the present invention, the cancer to be prevented, ameliorated or treated may be a solid tumor consisting of a mass generated by abnormal growth of cells in a solid organ, and may be divided, according to the solid organ, into gastric cancer, liver cancer, glioblastoma, ovarian cancer, colorectal cancer, head and neck cancer, bladder cancer, renal cell cancer, breast cancer, metastatic cancer, prostate cancer, pancreatic cancer, bile duct cancer, melanoma or lung cancer, which expresses carcinoembryonic antigen (CEA).

As used herein, the term "prevention" refers to any action of inhibiting or delaying the progression of cancer by administration of the composition of the present invention.

As used herein, the terms "treatment" and "alleviation" refer to any action of alleviating or beneficially changing symptoms of cancer by administration of the composition of the present invention.

For administration, the pharmaceutical composition of the present invention may be formulated as a pharmaceutical composition containing one or more pharmaceutically acceptable carriers in addition to the active ingredient described. As the pharmaceutically acceptable carriers, saline, sterile water, Ringer's solution, buffered saline, dextrose solution, maltodextrin solution, glycerol, ethanol, liposome, and a mixture of one or more of these components may be used, and if necessary, other conventional additives such as antioxidants, buffers, and bacteriostatic agents may be added. In addition, diluents, dispersants, surfactants, binders and lubricants may be additionally added to prepare injectable formulations such as aqueous solutions, suspensions or emulsions, as well as pills, capsules, granules or tablets. In addition, a target organ-specific antibody or other ligand may be used in combination with the carrier so as to act specifically on the target organ. Furthermore, the pharmaceutical composition may preferably be formulated depending on each disease or components using an appropriate method known in the art or using a method disclosed in Remington's Pharmaceutical Science (the latest edition), Mack Publishing Company, Easton Pa.

The pharmaceutical composition of the present invention may be a solution, suspension, dispersion, emulsion, gel, injectable liquid, or sustained-release formulation of the active ingredient. Preferably, the pharmaceutical composition may be an injectable liquid formulation.

When the pharmaceutical composition of the present invention is formulated as an injectable formulation, it may be prepared as a physically or chemically very stable injectable formulation by adjusting the pH with an aqueous acid solution or a buffer such as a phosphate buffer, which may be used for injection, in order to ensure the stability of the injectable formulation during distribution.

More specifically, the injectable formulation may be prepared by dissolving the composition in water for injection together with a stabilizing agent or solubilizing agent, and then sterilizing the solution by high-temperature sterilization under reduced pressure or by aseptic filtration. As the water for injection, distilled water for injection or a buffer for injection, for example, a phosphate buffer (pH 3.5 to 7.5) or sodium dihydrogen phosphate ($NaH_2PO_4$)-citrate buffer may be used. The phosphate used may be in the form of sodium salt, potassium salt, anhydride or hydrate, and may also be in the form of citrate, anhydride or hydrate.

In addition, the stabilizing agent that is used in the present invention includes sodium pyrosulfite, sodium bisulfite ($NaHSO_3$), sodium metabisulfite ($Na_2S_2O_3$) or ethylenediaminetetraacetic acid, and the solubilizing agent includes a base such as sodium hydroxide (NaOH), sodium hydrogen carbonate ($NaHCO_3$), sodium carbonate ($NaCO_3$) or potassium hydroxide (KOH), or an acid such as hydrochloric acid (HCl) or acetic acid ($CH_3COOH$).

The injectable formulation according to the present invention may be prepared to be bioabsorbable, biodegradable, biocompatible. "Bioabsorbable" means that the injectable formulation is capable of disappearing from its initial application site in the body, with or without degradation of the dispersed injectable formulation. "Biodegradable" means that the injectable formulation is capable of breaking down or degrading within the body, by hydrolysis or enzymatic degradation. "Biocompatible" means that all of the components are nontoxic in the body.

The injectable formulation according to the present invention may be prepared using conventional diluents, such as fillers, extenders, binders, wetting agents and surfactants, or excipients.

The composition or active ingredient of the present invention may be administered using a conventional method by an intravenous, intra-arterial, intraperitoneal, intramuscular, intrasternal, transdermal, intranasal, subcutaneous, intrauterine, intradural, inhalation, topical, intrarectal, oral, intraocular or intradermal route depending on the intended use. Preferably, it may be administered intravenously. The composition or active ingredient of the present invention may be administered by injection or catheter.

In the pharmaceutical composition of the present invention, the dose of the active ingredient contained in the pharmaceutical composition may be adjusted within the range of $1\times10$ to $1\times10^{50}$ transformed host cells/kg, preferably $1\times10$ to $1\times10^{30}$ transformed host cells/kg, more preferably $1\times10^{5}$ to $1\times10^{20}$ transformed host cells/kg, most preferably $1\times10^{7}$ to $1\times10^{9}$ transformed host cells/kg, for an adult weighing 60 kg. However, the optimal dose can be easily determined by those skilled in the art, and may vary depending on various factors, including the kind of disease, the severity of the disease, the contents of the active ingredient and other components in the composition, the type of the formulation, and the patient's age, body weight, general health condition, sex and diet, the time of administration, the route of administration, the secretion rate of the composition, the duration of treatment, and a particular drug which is used in combination with the composition.

In the pharmaceutical composition of the present invention, the active ingredient may be contained in an amount of 0.001 to 50 wt % based on the total weight of the composition. However, the content of the active ingredient is not limited thereto.

In addition, the pharmaceutical composition of the present invention may further contain at least one anticancer drug.

In the present invention, the anticancer drug may be at least one selected from the group consisting of nitrogen mustard, imatinib, oxaliplatin, rituximab, erlotinib, neratinib, lapatinib, gefitinib, vandetanib, nirotinib, semasanib, bosutinib, axitinib, cediranib, lestaurtinib, trastuzumab, gefitinib, bortezomib, sunitinib, carboplatin, bevacizumab, cisplatin, cetuximab, viscumalbum, asparaginase, tretinoin, hydroxycarbamide, dasatinib, estramustine, gemtuzumab ozogamicin, ibritumomab tusetan, heptaplatin, methylaminolevulinic acid, amsacrine, alemtuzumab, procarbazine, alprostadil, holmium nitrate chitosan, gemcitabine, doxyfluridine, pemetrexed, tegafur, capecitabine, gimeracin, oteracil, azacitidine, methotrexate, uracil, cytarabine, fluorouracil, fludagabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretonine, exemestane, aminoglutethimide, anagrelide, navelbine, fadrazol, tamoxifen, toremifen, testolactone, anastrozole, letrozole, vorozole, bicalutamide, lomustine, and carmustine, without being limited thereto.

Still another further embodiment of the present invention is directed to a method for preventing or treating cancer, the method comprising a step of administering, to a subject, the chimeric antigen receptor, polynucleotide, expression cassette, vector, host cell, polypeptide expressed from the host cell, or pharmaceutical composition, provided in the present invention.

As used herein, the term "subject" refers to any animals, including humans, monkeys, cows, horses, sheep, pigs, chickens, turkeys, quails, cats, dogs, mice, rats, rabbits or guinea pigs that have or are likely to develop cancer. The kind of subject is not particularly limited as long as the disease can be effectively prevented or treated by administering the pharmaceutical composition of the present invention to the subject.

The method of the present invention may further comprise a step of administering at least one anticancer drug to the subject.

In the method of the present invention, the administration dose, the administration method, and the definition of cancer and anticancer drug, etc. overlap with those described above with respect to the pharmaceutical composition, and description thereof will be omitted to avoid excessive complexity of the specification.

Hereinafter, the present invention will be described in detail with reference to the following examples. However, the following examples are merely illustrative of the present invention, and the scope of the present invention is not limited by the following examples.

Examples

[Example 1] Construction of Lenti-anti-CEA h(BBζ)-EGFRt-2$^{nd}$-CAR

A chimeric antigen receptor cassette consisting of EF-1α promoter-CD16 extracellular domain-CD8 hinge-CD8 transmembrane domain-4-1BB-CD3ζ-T2A-EGFRt set forth in SEQ ID NO: 18 was constructed. As shown in FIG. 3, the cassette was then inserted into the 3 prime position of the EF-1α promoter of the self-inactivating pCAR-EGFRt lentiviral vector. Thereafter, in order to check whether the chimeric antigen receptor cassette was properly inserted into the vector, the vector was digested with EcoR1/BamH1 restriction enzymes and then subjected to gel electrophoresis. As a result, as shown in FIG. 4, the band indicating the digestion and separation of the inserted receptor cassette could be seen. As shown in FIG. 4, it could be confirmed that the band indicating the digestion of the receptor-CD8-4-1BB-CD3ζ-EGFRt portion by the EcoR1/BamH1 restriction enzymes and the disappearance of the restriction enzyme sites during insertion into the pCAR-EGFTt appeared.

[Example 2] Analysis of Expression of CEA in Various Cancer Cell Lines

The following experiment was conducted to examine whether the cell membrane antigen CEA targeted by the chimeric antigen receptor constructed in Example 1 was expressed in pancreatic cancer cell lines (Bxpc3, Capan2, Cfpac, Hpac, Miapaca2, and Panel), bile duct cancer cell lines (HuCCT1 and SNU1196), and colorectal cancer cell lines (HT29 and HCT119), among human cancer cell lines expressing the antigen CEA. The cancer cells of each of the above-described cancer cell lines were cultured and then incubated with a 1:500 dilution of CEA-specific primary antibody. The cells were washed 3 times with PBS solution, and then incubated with Alexa488-conjugated secondary antibody, and the expression levels of CEA in the cells were measured by flow cytometry. The results are shown in FIG. 5.

As shown in FIG. 5, it could be confirmed that the antigen CEA was expressed in various cancer cells, including pancreatic cancer cells, biliary tract cancer cells and colorectal cancer cells. Thereby, it could be confirmed that the CAR T or CAR NK cells targeting CEA according to the present invention may be used for the purpose of preventing, alleviating or treating various cancers expressing CEA.

[Example 3] Construction of T Cells (Anti-CEA CAR-T Cells) Expressing Chimeric Antigen Receptor Targeting Cell Membrane Antigen CEA For the generation of a lentivirus to be used for transduction, Lenti-X 293 FT cells ($1\times10^6$) with the highest yield were inoculated and cultured overnight. After culture, the cells were transformed with the Lenti-anti-CEA-h(BBc)-EGFRt-2$^6$d-CAR plasmid (constructed in Example 1) using the lipofectamine 3000 transduction kit and cultured for 48 hours so that lentivirus was generated in the 293 FT cells.

The T cells isolated from peripheral blood were activated using CD3/CD28 macs beads and cultured for 24 hours. The T cells before and after activation were observed under a microscope at low magnification (left of FIG. 6) and high magnification (right of FIG. 6), and the results are shown in FIG. 6.

As shown in the microscopic images at the bottom of FIG. 6, it can be confirmed that, unlike the T cells that were not activated because the plasmid was not inserted therein, a large amount of activated T cells were transduced with the plasmid and cultured as shown in the microscopic images at the top of FIG. 6. After transduction, cells expressing EGFRt could be identified by performing flow cytometry for the expression of EGFR mounted on the chimeric antigen receptor cassette.

[Example 4] Evaluation of Cancer Cell Cytotoxicity of CAR T-Cells Transformed with Lenti-Anti-CEA-h(BBC)-EGFRt-2nd-CAR Plasmid 1. Analysis of Expression of Cell Membrane Antigen CEA in Cancer Cells A process in which a cancer cell line expressing CEA is attacked and killed by the CAR T-cells constructed according to the Example of the present invention was observed under a fluorescence microscope. An experiment for observing this process is as follows. $1\times10^4$ colorectal cancer HT29 cells were dispensed on a 1×2-cm chamber slide, adhesion of the cells to the chamber bottom was induced, and then immunofluorescence staining was performed. In this case, a 1:500 dilution of CEA-specific antibody was used in the experiment, and the cells were washed three times with PBS solution, and an FITC-conjugated antibody (1:500 dilution) was used as a secondary antibody for binding to the primary antibody. Then, the cells were observed under a fluorescence microscope, and the results are shown in FIG. 7.

As shown in FIG. 7, it could be confirmed that CEA was expressed in more than 90% of the HT29 cells.

2. Anticancer Effect Evaluation (1)

A process in which anti-CEA CAR T-cells inserted with the chimeric antigen receptor cassette targeting the antigen CEA kill (destroy) the colorectal cancer HT29 cells shown in FIG. 7 was observed under a fluorescence microscope, and the results are shown in FIG. 8.

As shown in FIG. 8, it could be confirmed that the cancer cell killing ability of the anti-CEA CAR T-cells into which the chimeric antigen receptor cassette targeting CEA has been inserted was significantly better than that of control T cells (T cells into which the chimeric antigen receptor cassette was not inserted) (see the difference in red fluorescence).

3. Anticancer Effect Evaluation (2)

In addition, a Non-RI cell cytotoxicity test was performed using HT29 and Capan1 cell lines expressing CEA, and the results are shown in FIGS. 9 and 10.

As shown in FIGS. 9 and 10, as a result of co-culturing anti-CEA CAR-T cells (effector): a cancer cell line (target cell line) at a ratio of 1:5, 1:1 and 5:1, it was confirmed that the anti-CEA CAR-T cells exhibited cell death rates of 6.7%, 20.3% and 65.0% at the co-culture ratios for the HT-29 cancer cell line, and exhibited cell death rates of 0.6%, 35.60% and 99.20% for the Capan-1 cell line, suggesting that the cell death rate increased in a concentration-dependent manner.

The above experimental results are in contrast to the insignificant cytotoxicity seen in the control T cells, and suggest that the anti-CEA CAR T-cells targeting CEA according to the present invention have effective cytotoxicity against a cancer cell line expressing the cell membrane antigen CEA.

From the experimental results of Examples 1 to 4, it could be seen that the expression cassette comprising the chimeric antigen receptor targeting CEA according to the present invention was stably inserted into high-purity T cells and expressed as a chimeric antigen receptor. In addition, it could be confirmed that the T cells inserted with the expression cassette according to the present invention had an excellent ability to kill cancer cells expressing the cell membrane antigen CEA, compared to control T cells into which the expression cassette was not inserted.

Although the present invention has been described in detail with reference to the specific features, it will be apparent to those skilled in the art that this detailed description is only of a preferred embodiment thereof, and does not limit the scope of the present invention. Thus, the substantial scope of the present invention will be defined by the appended claims and equivalents thereto.

Industrial Applicability

The present invention relates to a novel chimeric antigen receptor targeting carcinoembryonic antigen (CEA) present in cancer cells, cells expressing the same, and prevention, alleviation and treatment of cancer using the same.

The invention claimed is:

1. A method for treating cancer in a subject, comprising intravenously administering to the subject a population of T cells expressing a chimeric antigen receptor targeting carcinoembryonic antigen (CEA), wherein the chimeric antigen receptor comprises a polypeptide having the amino acid sequence of SEQ ID NO: 9 or 10, wherein the cancer is CEA-expressing pancreatic cancer.

* * * * *